(12) United States Patent
Lant et al.

(10) Patent No.: US 10,513,671 B2
(45) Date of Patent: Dec. 24, 2019

(54) METHOD OF TREATING A FABRIC

(71) Applicant: The Procter & Gamble Company, Cincinnati, OH (US)

(72) Inventors: Neil Joseph Lant, Newcastle upon Tyne (GB); Rebecca Louise Wood, North Shields (GB); Jeremie Robert Marcel Gummel, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 307 days.

(21) Appl. No.: 15/139,355

(22) Filed: Apr. 27, 2016

(65) Prior Publication Data

US 2016/0319226 A1    Nov. 3, 2016

(30) Foreign Application Priority Data

Apr. 29, 2015  (EP) .................................... 15165814
Oct. 15, 2015  (EP) .................................... 15190045

(51) Int. Cl.
*C11D 3/386*      (2006.01)

(52) U.S. Cl.
CPC .. *C11D 3/38636* (2013.01); *C12Y 301/21001* (2013.01); *C12Y 301/30002* (2013.01); *C12Y 302/01052* (2013.01)

(58) Field of Classification Search
None
See application file for complete search history.

(56) References Cited

U.S. PATENT DOCUMENTS

| | | |
|---|---|---|
| 5,599,786 A | 2/1997 | Siklosi et al. |
| 6,174,852 B1 | 1/2001 | Hayashi et al. |
| 9,139,798 B2 | 9/2015 | Holzhauer et al. |
| 2013/0072413 A1 | 3/2013 | Urbin et al. |
| 2014/0031272 A1 | 1/2014 | Shipovskov et al. |
| 2015/0299623 A1 | 10/2015 | Gori et al. |

FOREIGN PATENT DOCUMENTS

| | | |
|---|---|---|
| GB | 1314381 A | 4/1973 |
| WO | WO 01/46512 A2 | 6/2001 |
| WO | WO 2011/163457 A1 | 12/2011 |
| WO | WO 2014/087011 | * 6/2014 |
| WO | WO 2015/155350 A1 | 10/2015 |
| WO | WO 2015/155351 A1 | 10/2015 |
| WO | WO 2015/181286 A1 | 12/2015 |

OTHER PUBLICATIONS

U.S. Appl. No. 15/139,356, filed Apr. 27, 2016, Neil Joseph Lant.
U.S. Appl. No. 15/139,362, filed Apr. 27, 2016, Neil Joseph Lant.
U.S. Appl. No. 15/139,368, filed Apr. 27, 2016, Neil Joseph Lant.
U.S. Appl. No. 15/139,373, filed Apr. 27, 2016, Neil Joseph Lant.
EP Search Report for Application No. 15165814.3-1358, dated Jul. 31, 2015, 5 pages.
EP Search Report for Application No. 15190045.3-1358, dated Apr. 4, 2016, 6 pages.
PCT Search Report for Application No. PCT/US2016/029479, dated Jul. 5, 2016, 12 pages.
EP Search Report for Application No. 15190046.1-1358, dated Apr. 4, 2016, 6 pages.
PCT Search Report for Application No. PCT/US2016/029507, dated Jul. 5, 2016, 12 pages.
PCT Search Report for Application No. PCT/US2016/029425, dated Jul. 5, 2016, 12 pages.

* cited by examiner

*Primary Examiner* — Richard G Hutson
(74) *Attorney, Agent, or Firm* — Andres E. Velarde; Melissa G. Krasovec

(57) ABSTRACT

Method for treating a hydrophobically-modified textile with an aqueous solution of a nuclease enzyme, preferably a deoxyribonuclease or ribonuclease enzyme, rinsing and drying the textile. Use of the finishing step for improved cleaning with an aqueous solution of a nuclease enzyme, preferably a deoxyribonuclease or ribonuclease enzyme.

14 Claims, No Drawings
Specification includes a Sequence Listing.

METHOD OF TREATING A FABRIC

FIELD OF INVENTION

This invention relates to methods of treating textile surfaces.

BACKGROUND OF THE INVENTION

Fabric whiteness is a constant challenge for laundry detergent manufacturers. A particular problem can be buildup of soils over time. This is problematic for both coloured and white fabrics but may be particularly noticeable on white or pale-coloured fabrics, for example around collars and cuffs where incomplete cleaning occurs. This can also be problematic as it may result in malodour. Many solutions may be considered by the laundry detergent manufacturer based on different cleaning technologies available, such as surfactants, bleaches and enzymes. Many different types of enzyme are available to the detergent formulator for cleaning different types of soils, such as lipases, proteases, amylases, cellulases, peroxygenases, aryl esterases, cutinases, pectinases, mannanases and deoxyribonucleases. However, there is still a need for a cleaning or treatment composition which provides improved removal of stubborn soils which tend to build up over time, and/or mitigate the risk of malodour.

SUMMARY OF THE INVENTION

This invention relates to a method of treating a textile comprising the steps of:
(i) providing a hydrophobically-modified textile;
(ii) contacting the textile from step (i) with an aqueous solution comprising a nuclease enzyme, preferably a deoxyribonuclease or ribonuclease enzyme, optionally rinsing and drying the textile.

The invention also relates to use of a finishing step providing an increase in the hydrophobicity of a textile surface relative to the untreated textile surface, to increase deposition of a nuclease enzyme in a subsequent aqueous laundering step in which the finished textile from step (i) is contacted with an aqueous solution comprising a nuclease enzyme, preferably a deoxyribonuclease or ribonuclease enzyme. Preferably the aqueous solution comprising the nuclease enzyme is provided by the addition of a laundry cleaning and/or treatment composition comprising the nuclease enzyme in the form of a cleaning and/or treatment composition. Preferably the cleaning and/or treatment composition is in the form of a water-soluble unit dose pouch, preferably a multi-compartment unit dose product, to water.

According to a further aspect of the invention there is provided a cleaning and/or treatment composition comprising a nuclease enzyme as defined herein and a glycosyl hydrolase from family GH20, preferably a β-N-acetylglucosaminidase enzyme from E.C. 3.2.1.52.

DETAILED DESCRIPTION OF THE INVENTION

Definitions

As used herein, the term "alkoxy" is intended to include C1-C8 alkoxy and C1-C8 alkoxy derivatives of polyols having repeating units such as butylene oxide, glycidol oxide, ethylene oxide or propylene oxide.

As used herein, unless otherwise specified, the terms "alkyl" and "alkyl capped" are intended to include C1-C18 alkyl groups, or even C1-C6 alkyl groups.

As used herein, unless otherwise specified, the term "aryl" is intended to include C3-12 aryl groups.

As used herein, unless otherwise specified, the term "arylalkyl" and "alkaryl" are equivalent and are each intended to include groups comprising an alkyl moiety bound to an aromatic moiety, typically having C1-C18 alkyl groups and, in one aspect, C1-C6 alkyl groups.

The terms "ethylene oxide," "propylene oxide" and "butylene oxide" may be shown herein by their typical designation of "EO," "PO" and "BO," respectively.

As used herein, the term "cleaning and/or treatment composition" includes, unless otherwise indicated, granular, powder, liquid, gel, paste, unit dose, bar form and/or flake type washing agents and/or fabric treatment compositions, including but not limited to products for laundering fabrics, fabric softening compositions, fabric enhancing compositions, fabric freshening compositions, and other products for the care and maintenance of fabrics, and combinations thereof. Such compositions may be pre-treatment compositions for use prior to a washing step or may be rinse added compositions, as well as cleaning auxiliaries, such as bleach additives and/or "stain-stick" or pre-treat compositions or substrate-laden products such as dryer added sheets.

As used herein, "cellulosic substrates" are intended to include any substrate which comprises cellulose, either 100% by weight cellulose or at least 20% by weight, or at least 30% by weight or at least 40 or at least 50% by weight or even at least 60% by weight cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Typically cellulosic substrates comprise cotton. Articles formed from cellulosic fibers include textile articles such as fabrics. Articles formed from pulp include paper.

As used herein, the term "maximum extinction coefficient" is intended to describe the molar extinction coefficient at the wavelength of maximum absorption (also referred to herein as the maximum wavelength), in the range of 400 nanometers to 750 nanometers.

As used herein "average molecular weight" is reported as an average molecular weight, as determined by its molecular weight distribution: as a consequence of their manufacturing process, polymers disclosed herein may contain a distribution of repeating units in their polymeric moiety.

As used herein the term "variant" refers to a polypeptide that contains an amino acid sequence that differs from a wild type or reference sequence. A variant polypeptide can differ from the wild type or reference sequence due to a deletion, insertion, or substitution of a nucleotide(s) relative to said reference or wild type nucleotide sequence. The reference or wild type sequence can be a full-length native polypeptide sequence or any other fragment of a full-length polypeptide sequence. A polypeptide variant generally has at least about 70% amino acid sequence identity with the reference sequence, but may include 75% amino acid sequence identity with the reference sequence, 80% amino acid sequence identity with the reference sequence, 85% amino acid sequence identity with the reference sequence, 86% amino acid sequence identity with the reference sequence, 87% amino acid sequence identity with the reference sequence, 88% amino acid sequence identity with the reference sequence, 89% amino acid sequence identity with the reference sequence, 90% amino acid sequence identity with the reference sequence, 91% amino acid sequence identity with the reference sequence, 92% amino acid sequence identity with the reference sequence, 93% amino acid sequence identity with the reference sequence, 94% amino acid sequence identity with the reference sequence, 95% amino acid sequence identity with the reference sequence, 96% amino acid sequence identity with the reference sequence, 97% amino acid sequence identity with the reference sequence, 98% amino acid sequence identity with the reference sequence, 98.5% amino acid sequence identity with the reference sequence or 99% amino acid sequence identity with the reference sequence.

As used herein, articles such as "a" and "an" when used in a claim, are understood to mean one or more of what is claimed or described.

As used herein, the terms "include/s" and "including" are meant to be non-limiting.

As used herein, the term "solid" includes granular, powder, bar and tablet product forms.

As used herein, the term "fluid" includes liquid, gel, paste and gas product forms.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

Hydrophobically-modified Textile

The hydrophobically-modified textile is a textile having thereon a finishing treatment which provides an increase in the hydrophobicity of the textile surface relative to the untreated textile surface. The hydrophobicity increase can be determined by measuring the water contact angle of the textile surface. "Water contact angle" means the angle measured through a liquid at which a liquid/vapor interface meets a solid surface. It quantifies the wettability of the solid surface by the liquid. The contact angle is a reflection of how strongly the liquid and solid molecules interact with each other, relative to how strongly each interacts with its own kind. On many highly hydrophilic surfaces such as cotton, water droplets will exhibit contact angles of between 0° to 30°. Generally, if the water contact angle is larger than 90°, the solid surface is considered hydrophobic. The analytical protocol is the contact angle measurement wherein a droplet of water is deposited on the surface and the angle of the interface measured through Drop Shape Analysis using one of many commercial instruments available for the purpose, such as those from Kruss, Hamburg, Germany. A specific standardized protocol to follow is defined by the American Society for Testing and Materials (protocol ASTM D7334-08).

Preferably the hydrophobic modification provides an increase in water contact angle of at least 20°, or more preferably at least 30°. When measured according to the method given above, the water contact angle of the textile surface after the finishing step is preferably at least 50°, or at least 60° or at least 70° or at least 80°, or even at least 90°.

Preferred textiles comprise cellulosic substrates, preferably comprising cotton. Preferably the cellulosic substrate comprises at least 40% by weight cellulose, preferably at least 50% by weight or at least 60% by weight cellulose. The hydrophobic modification step is typically provided by a chemical surface treatment applied to the surface of the textile fibres or yarns prior to forming into a fabric, or to the textile surface in the form of fabric. The hydrophobic modification may be provided by a chemical finish selected from a soil-release agent, a soil repellent, a thermal regulator, a softener, a flame-retardant, an anti-static agent, a shrink retardant, a durable-press coating, a self-cleaning agent and an anti-odor agent, which increases the hydrophobicity of the textile surface.

The hydrophobic modification of the textile surface by applying a coating selected from the group consisting of cationic compounds, silicones, paraffins, fluorinated compounds and mixtures thereof. The chemical modification may comprise treatment with an enzyme The chemical modification may use any of the conventional textile treatment methods such as padding, exhaustion, coating, spraying, foam application and plasma-enhanced chemical vapour deposition. Nanotechnology can also be used.

Preferably in the finishing step the textile surface is chemically modified by deposition of a cationic compound and/or silicone compound and/or fluorocarbon and/or paraffin or mixtures thereof. Examples of suitable hydrophobic finishes are given in Chapters 4 and 13 of Paul, R., *Functional Finishes for Textiles,* 1st Edition, Elsevier, 2014, ISBN-9780857098399.

These include softening finishes such as cationic softeners (e.g. amine salts, imidazolines, ester quats), nonionic softeners (e.g. polyethylenes, glycerol monostearate, ethoxylates of fatty acids, fatty amines, castor oil, fatty alcohol, fatty esters), silicone softeners (e.g. polydimethyl siloxane (PDMS), polymethyl hydrogen siloxane (PMHS), aminofunctional silicone, epoxysilicone, and amidosilicones and mixtures thereof.

Other hydrophobic finishes include fluorocarbons which have to be solved or dispersed to gain a finishing agent which can be applied by conventional dipping and padding processes. Fluorocarbons can be used to achieve both water- and oil-repellency, e.g. through use of polymers with perfluorinated alkyl side chains. Perfluorinated alkylsilane modified with different groups acting as anchor groups can be used for fixation onto hydrophilic hydroxyl group-bearing fibres such as cotton.

Hydrophobic finishing can also be achieved with plasma treatments such as plasma polymerisation and sputtering. Typical monomers used to create hydrophobic effects in plasma polymerization are hexamethyldisiloxane, vinyltrimethylsilane and 2-(perfluorohexyl)ethyl acrylate.

Introducing a nanostructure onto textile fibres results can also be used to achieve a hydrophobic finish, resulting in high contact angles, similar to other substrates with nanostructured surfaces such as metal, ceramics or glass. These surfaces are also called superhydrophobic surfaces or self-cleaning surfaces. Silica particles, silver particles and calcium carbonate (CaCO3) can be used to achieve nanostructured textiles. These inorganic materials are used in combination with the polymers poly(glycidyl methacrylate) (PGMA) and poly(styrene-b-ethylene-co-butylene-b-styrene) (SEBS) as hydrophobic component.

Other suitable hydrophobic finishing agents include dendrimers, carbon nanotubes, hydrophobins and sol-gel materials.

Specific examples of suitable commercial textile finishes include fluorinated lattices (e.g. Foraperle™ 503; F-503 from Elf Atochem, Oleophobol™ C; O1-C from Huntsman), fluorocarbons (e.g. Oleophobol™ SL-A; 7713/SM from Huntsman), fluoroalkyl functional polysiloxane (e.g. Dynasylan™ F8815 from Evonik), perfluoro-acrylic copolymers (e.g. Repellan™ EM; EPF; NFC from Pulcra), conventional fluorocarbon—CF8 chemistry (e.g. RUCO-Guard™ AFR from Rudolf GmbH, fluorocarbons (e.g. Fluorepel™ OWS from Cytonix, Dipolit™ 97105 from Oztek Stampa Textile Company, Nuva™ 2110 from Archroma, RUCOSTAR™ ACT6 from Rudolf GmbH), fluorocarbon resins (e.g. Asahi Guard™ AG-480 from Asahi, Anthydrin™ from Zschimmer & Schwarz), and dendrimers (e.g. RUCO-DRY ECO™ from Rudolf GmbH).

The inventors of the present invention have found that surprisingly the deposition of the nuclease enzyme is increased by increasing the hydrophobicity of the textile surface, leading to increased efficacy.

Optionally the finished textile surface may be washed and rinsed prior to the second step as long as the textile surface retains increased hydrophobicity relative to the untreated textile surface.

The hydrophobically-modified textile is contacted with an aqueous solution comprising a nuclease enzyme. The aqueous solution may comprise nuclease enzyme alone. However, preferably the aqueous solution also additionally comprises surfactant, preferably in an amount from 0.005 g/l to 5 g/l of surfactant or from 0.1 to 3 g/l or to 2 g/l. Preferably the aqueous solution comprising the nuclease enzyme is provided by the addition of a nuclease enzyme-containing laundry cleaning and/or treatment composition to water in a laundering step. The cleaning and/or treatment composition will comprise in addition to the nuclease enzyme, any of the additional adjunct materials from such a cleaning and/or treatment composition, as described below.

Nuclease Enzyme

The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof.

Nucleases in class E.C. 3.1.21.x cleave at the 3' hydroxyl to liberate 5' phosphomonoesters as follows:

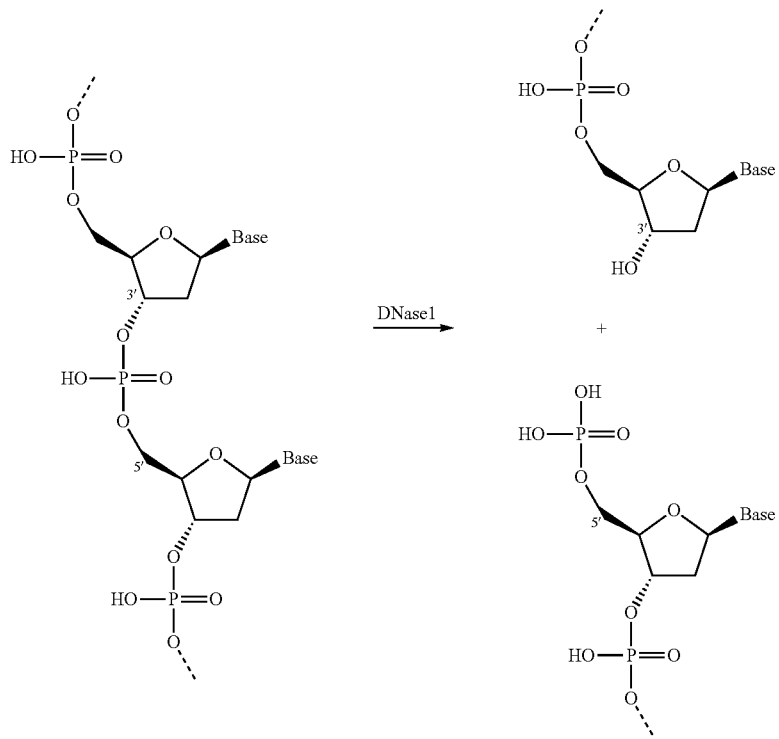

Nuclease enzymes from class E.C. 3.1.21.x and especially where x=1 are particularly preferred.

Nucleases in class E.C. 3.1.22.y cleave at the 5' hydroxyl to liberate 3' phosphomonoesters. Enzymes in class E.C. 3.1.30.z may be preferred as they act on both DNA and RNA and liberate 5'-phosphomonoesters. Suitable examples from class E.C. 3.1.31.2 are described in US2012/0135498A, such as SEQ ID NO:3 therein. Such enzymes are commercially available as DENARASE® enzyme from c-LECTA.

Nuclease enzymes from class E.C. 3.1.31.1 produce 3' phosphomonoesters.

Preferably, the nuclease enzyme comprises a microbial enzyme. The nuclease enzyme may be fungal or bacterial in origin. Bacterial nucleases may be most preferred. Fungal nucleases may be most preferred.

The microbial nuclease is obtainable from *Bacillus*, such as a *Bacillus licheniformis* or *Bacillus subtilis* bacterial nucleases. A preferred nuclease is obtainable from *Bacillus licheniformis*, preferably from strain EI-34-6. A preferred deoxyribonuclease is a variant of *Bacillus licheniformis*, from strain EI-34-6 nucB deoxyribonuclease defined in SEQ ID NO:1 herein, or variant thereof, for example having at least 70% or 75% or 80% or 85% or 90% or 95%, 96%, 97%, 98%, 99% or 100% identical thereto.

Other suitable nucleases are defined in SEQ ID NO:2 herein, or variant thereof, for example having at least 70% or 75% or 80% or 85% or 90% or 95%, 96%, 97%, 98%, 99% or 100% identical thereto. Other suitable nucleases are defined in SEQ ID NO:3 herein, or variant thereof, for example having at least 70% or 75% or 80% or 85% or 90% or 95%, 96%, 97%, 98%, 99% or 100% identical thereto.

A fungal nuclease is obtainable from *Aspergillus*, for example *Aspergillus oryzae*. A preferred nuclease is obtainable from *Aspergillus oryzae* defined in SEQ ID NO: 5 herein, or variant thereof, for example having at least 60% or 70% or 75% or 80% or 85% or 90% or 95%, 96%, 97%, 98%, 99% or 100% identical thereto.

Another suitable fungal nuclease is obtainable from *Trichoderma*, for example *Trichoderma harzianum*. A preferred nuclease is obtainable from *Trichoderma harzianum* defined in SEQ ID NO: 6 herein, or variant thereof, for example having at least 60% or 70% or75% or 80% or 85% or 90% or 95%, 96%, 97%, 98%, 99% or 100% identical thereto.

Other fungal nucleases include those encoded by the DNA sequences of *Aspergillus oryzae* RIB40, *Aspergillus oryzae* 3.042, *Aspergillus flavus* NRRL3357, *Aspergillus parasiticus* SU-1, *Aspergillus nomius* NRRL13137, *Trichoderma reesei* QM6a, *Trichoderma virens* Gv29-8, *Oidiodendron maius* Zn, *Metarhizium guizhouense* ARSEF 977, *Metarhizium majus* ARSEF 297, *Metarhizium robertsii* ARSEF 23, *Metarhizium acridum* CQMa 102, *Metarhizium brunneum* ARSEF 3297, *Metarhizium anisopliae*, *Colletotrichum fioriniae* PJ7, *Colletotrichum sublineola*, *Trichoderma atroviride* IMI 206040, *Tolypocladium ophioglossoides* CBS 100239, *Beauveria bassiana* ARSEF 2860, *Colletotrichum higginsianum*, *Hirsutella minnesotensis* 3608, *Scedosporium apiospermum*, *Phaeomoniella chlamydospora*, *Fusarium verticillioides* 7600, *Fusarium oxysporum* f. sp. *cubense* race 4, *Colletotrichum graminicola* M1.001, *Fusarium oxysporum* FOSC 3-a, *Fusarium avenaceum*, *Fusarium langsethiae*, *Grosmannia clavigera* kw1407, *Claviceps purpurea* 20.1, *Verticillium longisporum*, *Fusarium oxysporum* f. sp. *cubense* race 1, *Magnaporthe oryzae* 70-15, *Beauveria bassiana* D1-5, *Fusarium pseudograminearum* CS3096, *Neonectria ditissima*, *Magnaporthiopsis poae* ATCC 64411, *Cordyceps militaris* CM01, *Marssonina brunnea* f. sp. 'multigermtubi' MB_m1, *Diaporthe ampelina*, *Metarhizium album* ARSEF 1941, *Colletotrichum gloeosporioides* Nara gc5, *Madurella mycetomatis*, *Metarhizium brunneum* ARSEF 3297, *Verticillium alfalfae* VaMs.102, *Gaeumannomyces graminis* var. *tritici* R3-111a-1, *Nectria haematococca* mpVI 77-13-4, *Verticillium longisporum*, *Verticillium dahliae* VdLs.17, *Torrubiella hemipterigena*, *Verticillium longisporum*, *Verticillium dahliae* VdLs.17, *Botrytis cinerea* B05.10, *Chaetomium globosum* CBS 148.51, *Metarhizium anisopliae*, *Stemphylium lycopersici*, *Sclerotinia borealis* F-4157, *Metarhizium robertsii* ARSEF 23, *Myceliophthora thermophila* ATCC 42464, *Phaeosphaeria nodorum* SN15, *Phialophora attae*, *Ustilaginoidea vixens*, *Diplodia seriata*, *Ophiostoma piceae* UAMH 11346, *Pseudogymnoascus pannorum* VKM F-4515 (FW-2607), *Bipolaris oryzae* ATCC 44560, *Metarhizium guizhouense* ARSEF 977, *Chaetomium thermophilum* var. *thermophilum* DSM 1495, *Pestalotiopsis fici* W106-1, *Bipolaris zeicola* 26-R-13, *Setosphaeria turcica* Et28A, *Arthroderma otae* CBS 113480 and *Pyrenophora tritici-repentis* Pt-1C-BFP.

Preferably the nuclease is an isolated nuclease.

Preferably the nuclease enzyme is present in the aqueous solution in an amount of from 0.01 ppm to 1000 ppm of the nuclease enzyme, or from 0.05 or from 0.1 ppm to 750 or 500 ppm.

The nucleases may also give rise to biofilm-disrupting effects.

In a preferred composition, the composition additionally comprises a β-N-acetylglucosaminidase enzyme from E.C. 3.2.1.52, preferably an enzyme having at least 70%, or at least 75% or at least 80% or at least 85% or at least 90% or at least 95% or at least 96% or at least 97% or at least 98% or at least 99% or at least or 100% identity to SEQ ID NO:4.

Cleaning and/or Treatment Adjunct Materials

When the aqueous solution is provided by the addition of a cleaning and/or treatment composition to water, in addition to the nuclease enzyme the cleaning and/or treatment composition will comprise optional cleaning and/or treatment adjunct materials. The nuclease enzyme will preferably be present in the composition in amounts of 0.00001% to about 3% by weight, from about 0.0001% to about 2% by weight or even from about 0.001% to about 1% by weight enzyme protein by weight of the composition.

Preferably the composition will additionally comprise a β-N-acetylglucosaminidase enzyme from E.C. 3.2.1.52, preferably an enzyme having at least 70%, or at least 75% or at least 80% or at least 85% or at least 90% or at least 95% or at least 96% or at least 97% or at least 98% or at least 99% or at least or 100% identity to SEQ ID NO: 4. When present, the β-N-acetylglucosaminidase enzyme will typically be present in an amount from 0.00001% to about 2%, from about 0.0001% to about 1% or even from about 0.001% to about 0.5% enzyme protein by weight of the composition.

Further suitable adjuncts may be, for example to assist or enhance cleaning performance, for treatment of the substrate to be cleaned, for example by softening or freshening, or to modify the aesthetics of the detergent composition as is the case with perfumes, colorants, non-fabric-shading dyes or the like. Suitable adjunct materials include, but are not limited to, surfactants, builders, chelating agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, additional brighteners, suds suppressors, dyes, hueing dyes, perfumes, perfume delivery systems, structure elasticizing agents, fabric softeners, carriers, hydrotropes, processing aids, solvents, additional dyes and/or pigments, some of which are discussed in more detail below. In addition to the disclosure below, suitable examples of such other adjuncts and levels of use are found in U.S. Pat. Nos. 5,576,282, 6,306,812 B1 and 6,326,348 B1 that are incorporated by reference.

Particularly preferred additional adjunct materials may be further enzymes.

Enzymes. Preferably the composition comprises one or more additional enzymes. Preferred enzymes provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A preferred combination of additional enzymes comprises a protease and a lipase, preferably in conjunction with amylase. When present in the composition, the aforementioned additional enzymes may each be present at levels from about 0.00001% to about 2%, from about 0.0001% to about 1% or even from about 0.001% to about 0.5% enzyme protein by weight of the composition.

Proteases. Preferably the composition comprises one or more proteases. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii* described in U.S. Pat. Nos. 6,312,936 B1, 5,679, 630, 4,760,025, 7,262,042 and WO09/021867.

(b) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(c) metalloproteases, including those derived from *Bacillus amyloliquefaciens* described in WO 07/044993A2.

Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)— all from Henkel/Kemira; and KAP (*Bacillus alkalophilus* subtilisin with mutations A230V+S256G+S259N) from Kao, or as disclosed in WO2009/149144, WO2009/149145, WO2010/56653, WO2010/56640, WO2011/072117, US2011/0237487, WO2011/140316, WO2012/151480, EP2510092, EP2566960 OR EP2705145.

Amylases. Preferably the composition may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in WO 94/02597, WO 94/18314, WO96/23874 and WO 97/43424, especially the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp.707 (SEQ ID NO:7 in U.S. Pat. No. 6,093,562), especially those comprising one or more of the following mutations M202, M208, 5255, R172, and/or M261. Preferably said amylase comprises one or more of M202L, M202V, M2025, M202T, M202I, M202Q, M202W, S255N and/or R172Q. Particularly preferred are those comprising the M202L or M202T mutations.

(e) variants described in WO 09/149130, preferably those exhibiting at least 90% identity with SEQ ID NO: 1 or SEQ ID NO:2 in WO 09/149130, the wild-type enzyme from *Geobacillus Stearophermophilus* or a truncated version thereof;

(f) variants as described in EP2540825 and EP2357220, EP2534233; (g) variants as described in WO2009100102 and WO2010115028.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

Lipases. Preferably the composition comprises one or more lipases, including "first cycle lipases" such as those described in U.S. Pat. No. 6,939,702 B1 and US PA 2009/0217464. Preferred lipases are first-wash lipases. In one embodiment of the invention the composition comprises a first wash lipase. First wash lipases includes a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15A of E1 or Q249 with a positively charged amino acid; and (c) comprises a peptide addition at the C-terminal; and/or (d) comprises a peptide addition at the N-terminal and/or (e) meets the following limitations: i) comprises a negative amino acid in position E210 of said wild-type lipase; ii) comprises a negatively charged amino acid in the region corresponding to positions 90-101 of said wild-type lipase; and iii) comprises a neutral or negative amino acid at a position corresponding to N94 or said wild-type lipase and/or has a negative or neutral net electric charge in the region corresponding to positions 90-101 of said wild-type lipase. Preferred are variants of the wild-type lipase from *Thermomyces lanuginosus* comprising one or more of the T231R and N233R mutations. The wild-type sequence is the 269 amino acids (amino acids 23-291) of the Swissprot accession number Swiss-Prot 059952 (derived from *Thermomyces lanuginosus* (*Humicola lanuginosa*)). Preferred lipases would include those sold under the tradenames Lipex® and Lipolex® and Lipoclean®. Other suitable lipases include those described in European Patent Application No. 12001034.3 or EP2623586.

Endoglucanases. Other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Pectate Lyases. Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Antimicrobials. It may be preferred for the compositions to comprise in addition, one or mixtures of more than one compounds which may give rise to anti-microbial effects. These may be standard ingredients of the treatment compositions that are added for cleaning or malodor benefits such as bleaching agents, but have some anti-microbial effect or they may be added specifically to provide anti-microbial effect. Suitable examples may include but are not limited to aldehydes (formaldehyde, glutaraldehyde, ortho-phtalaldehyde), sulphur dioxide, sulphites, bisulphites, vanillic acid esters), chlorine and oxygen based oxidizing agents (sodium and calcium hypochlorite or hypobromite, chloramine and chloramine-T, chlorine dioxide, hydrogen peroxide, iodine, ozone, peracetic acid, performic acid, potassium permanganate, potassium peroxymonosulfate), phenolics (phenol, o-phenylphenol, chloroxylenol, hexachlorophene, thymol, amylmetacresol, 2,4-dichlorobenzyl alcohol, policresylen, fentichlor, 4-allylcatechol, p-hydroxybenzoic acid esters including benzylparaben, butylparaben, ethylparaben, methtlparaben and propylparaben, butylated hydroxyanisole, butylated hydroxytoluene, capaicin, carvacrol, creosol, eugenol, guaiacol), halogenated (hydroxy)diphenylethers (diclosan, triclosan, hexachlorophene and bromochlorophene, 4-hexylresorcinol, 8-hydroxyquinoline and salts thereof), quaternary ammonium compounds (benzalkonium chloride derivatives, benzethonium chloride derivatives, cetrimonium chloride/bromide, cetylpyridinium, cetrimide, benzoxonium chloride, didecyldimethyl ammonium chloride), acridine derivatives (ethacridine lactate, 9-aminoacridine, euflavine), biguanides including polymeric biguanides, and amidines (polyaminopropyl biguanide, dibrompropamidine, chlorhexidine, alexidine, propamidine, hexamidine, polihexanide), nitrofuran derivatives (nitrofurazone), quinoline derivatives (dequalinium, chlorquinaldol, oxyquinoline, clioquinol), iodine products, essential oils (bay, cinnamon, clove, thyme, eucalyptus, peppermint, lemon, tea tree, magnolia extract, menthol, geraniol), cations, Anilides (saclicylanilide, Diphenylureas), salicylic acid esters including menthyl salicylate, methyl salicylate and phenyl salicylate, pyrocatechol, phtalic acid and salts thereof, hexetidine, octenidine, sanguinarine, domiphen bromide, alkylpyridinium chlorides such as cetylpyridinium chloride, tetradecylpyridinium chloride and N-tetradecyl-4-ethylpyridinium chloride, iodine, sulfonamides, piperidino derivatives such as delmopinol and octapinol, and mixtures thereof, miscellaneous preservatives (derivatives of 1,3-dioxane, derivatives of imidazole, Isothizolones, derivatives of hexamine, triazines, oxazolo-oxazoles, sodium hydroxymethylglycinate, methylene bisthiocyanate, captan).

Preferred antibacterial systems are halogenated benzyl alcohol derivatives such as chloroxylenol (PCMX), halogenated hydroxydiphenylethers preferably diclosan, quaternary ammonium salts preferably alkylbenzalkonium and alkylbenzethonium chloride and derivatives thereof, essential oils, bleach system preferably a peroxide bleach, and mixtures thereof. Most preferred antibacterial systems are benzalkonium chloride, diclosan and PCMX.

Encapsulates. The composition may comprise an encapsulate, for example an encapsulate comprising a core, a shell having an inner and outer surface, said shell encapsulating said core. The core may comprise any laundry care adjunct, though typically the core may comprise material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof. Preferred encapsulates comprise perfume. Preferred encapsulates comprise a shell which may comprise melamine formaldehyde and/or cross linked melamine formaldehyde. Preferred encapsulates comprise a core material and a shell, said shell at least partially surrounding said core material, is disclosed. At least 75%, 85% or even 90% of said encapsulates may have a fracture strength of from 0.2 MPa to 10 MPa, and a benefit agent leakage of from 0% to 20%, or even less than 10% or 5% based on total initial encapsulated benefit agent. Preferred are those in which at least 75%, 85% or even 90% of said encapsulates may have (i) a particle size of from 1 microns to 80 microns, 5 microns to 60 microns, from 10 microns to 50 microns, or even from 15 microns to 40 microns, and/or (ii) at least 75%, 85% or even 90% of said encapsulates may have a particle wall thickness of from 30 nm to 250 nm, from 80 nm to 180 nm, or even from 100 nm to 160 nm. Formaldehyde scavengers may be employed with the encapsulates, for example, in a capsule slurry and/or added to a composition before, during or after the encapsulates are added to such composition. Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In a preferred aspect the composition may comprise a deposition aid, preferably in addition to encapsulates. Preferred deposition aids are selected from the group consisting of cationic and nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or more monomers selected from the group comprising acrylic acid and acrylamide.

Perfume. Preferred compositions of the invention comprise perfume. Typically the composition comprises a perfume that comprises one or more perfume raw materials, selected from the group as described in WO08/87497. However, any perfume useful in a detergent may be used. A preferred method of incorporating perfume into the compositions of the invention is via an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix. In a further aspect the perfume may be pre-complexed with a polyamine, preferably a polyethylenimine so as to form a Schiff base.

Polymers. The detergent composition may comprise one or more polymers in addition to the DTI which may be polymeric. Examples are optionally modified carboxymethylcellulose, poly (ethylene glycol), poly(vinyl alcohol), polycarboxylates such as polyacrylates, maleic/acrylic acid copolymers and lauryl methacrylate/acrylic acid co-polymers and carboxylate polymers.

Suitable carboxylate polymers include maleate/acrylate random copolymer or polyacrylate homopolymer. The carboxylate polymer may be a polyacrylate homopolymer having a molecular weight of from 4,000 Da to 9,000 Da, or from 6,000 Da to 9,000 Da. Other suitable carboxylate polymers are co-polymers of maleic acid and acrylic acid, and may have a molecular weight in the range of from 4,000 Da to 90,000 Da.

Other suitable carboxylate polymers are co-polymers comprising: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or C1 to C20 organic group;

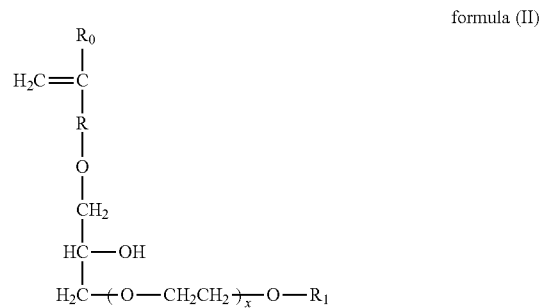

formula (II)

in formula (II), $R_0$ represents a hydrogen atom or $CH_3$ group, R represents a $CH_2$ group, $CH_2CH_2$ group or single bond, X represents a number 0-5, and $R_1$ is a hydrogen atom or C1 to C20 organic group.

The composition may comprise one or more amphiphilic cleaning polymers such as the compound having the following general structure: bis(($C_2H_5O)(C_2H_4O)n)(CH_3$)—$N^+$—$C_xH_{2x}$—$N^+$—$(CH_3)$-bis(($C_2H_5O)(C_2H_4O)n)$, wherein n=from 20 to 30, and x=from 3 to 8, or sulphated or sulphonated variants thereof. In one aspect, this polymer is sulphated or sulphonated to provide a zwitterionic soil suspension polymer.

The composition preferably comprises amphiphilic alkoxylated grease cleaning polymers which have balanced hydrophilic and properties such that they remove grease particles from fabrics and surfaces. Preferred amphiphilic alkoxylated grease cleaning polymers comprise a core structure and a plurality of alkoxylate groups attached to that core structure. These may comprise alkoxylated polyalkylenimines, preferably having an inner polyethylene oxide block and an outer polypropylene oxide block. Typically these may be incorporated into the compositions of the invention in amounts of from 0.005 to 10 wt %, generally from 0.5 to 8 wt %.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —(CH$_2$CH$_2$O)$_m$ (CH$_2$)$_n$CH$_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

The composition may comprise polyethylene glycol polymers and these may be particularly preferred in compositions comprising mixed surfactant systems. Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22.

Typically these are incorporated into the compositions of the invention in amounts from 0.005 to 10 wt %, more usually from 0.05 to 8 wt %.

Preferably the composition comprises one or more carboxylate polymer, such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da. Typically these are incorporated into the compositions of the invention in amounts from 0.005 to 10 wt %, or from 0.05 to 8 wt %.

Preferably the composition comprises one or more soil release polymers. Examples include soil release polymers having a structure as defined by one of the following Formulae (VI), (VII) or (VIII):

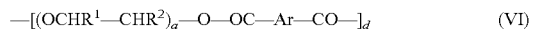
(VI)

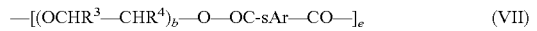
(VII)

(VIII)

wherein:
a, b and c are from 1 to 200;
d, e and f are from 1 to 50;
Ar is a 1,4-substituted phenylene;
sAr is 1,3-substituted phenylene substituted in position 5 with SO$_3$Me;
Me is Li, K, Mg/2, Ca/2, Al/3, ammonium, mono-, di-, tri-, or tetraalkylammonium wherein the alkyl groups are C$_1$-C$_{18}$ alkyl or C$_2$-C$_{10}$ hydroxyalkyl, or mixtures thereof;
R$^1$, R$^2$, R$^3$, R$^4$, R$^5$ and R$^6$ are independently selected from H or C$_1$-C$_{18}$ n- or iso-alkyl; and R$^7$ is a linear or branched C$_1$-C$_{18}$ alkyl, or a linear or branched C$_2$-C$_{30}$ alkenyl, or a cycloalkyl group with 5 to 9 carbon atoms, or a C$_8$-C$_{30}$ aryl group, or a C$_6$-C$_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clamant. Other suitable soil release polymers are Marloquest polymers, such as Marloquest SL supplied by Sasol.

Preferably the composition comprises one or more cellulosic polymer, including those selected from alkyl cellulose, alkyl alkoxyalkyl cellulose, carboxyalkyl cellulose, alkyl carboxyalkyl cellulose. Preferred cellulosic polymers are selected from the group comprising carboxymethyl cellulose, methyl cellulose, methyl hydroxyethyl cellulose, methyl carboxymethyl cellulose, and mixures thereof. In one aspect, the carboxymethyl cellulose has a degree of carboxymethyl substitution from 0.5 to 0.9 and a molecular weight from 100,000 Da to 300,000 Da.

Bleaching Agents. It may be preferred for the composition to comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent or mixtures of bleaching agents by weight of the subject composition. Examples of suitable bleaching agents include:

(1) photobleaches for example sulfonated zinc phthalocyanine sulfonated aluminium phthalocyanines, xanthene dyes and mixtures thereof;

(2) pre-formed peracids: Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof. Suitable examples include peroxycarboxylic acids or salts thereof, or peroxysulphonic acids or salts thereof. Typical peroxycarboxylic acid salts suitable for use herein have a chemical structure corresponding to the following chemical formula:

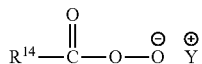

wherein: R$^{14}$ is selected from alkyl, aralkyl, cycloalkyl, aryl or heterocyclic groups; the R$^{14}$ group can be linear or branched, substituted or unsubstituted; having, when the peracid is, from 6 to 14 carbon atoms, or from 8 to 12 carbon atoms and, when the peracid is hydrophilic, less than 6 carbon atoms or even less than 4 carbon atoms and Y is any suitable counter-ion that achieves electric charge neutrality, preferably Y is selected from hydrogen, sodium or potassium. Preferably, R$^{14}$ is a linear or branched, substituted or unsubstituted C$_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimidoperoxy-alkanoic acids, in particular ε-phthalimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

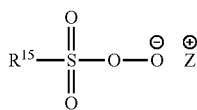

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{4-14}$, preferably $C_{6-14}$ alkyl. Preferably such bleach components may be present in the compositions of the invention in an amount from 0.01 to 50%, most preferably from 0.1% to 20%.

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C═O)-L wherein R is an alkyl group, optionally branched, having, when the bleach activator is, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5, 5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject composition may comprise NOBS, TAED or mixtures thereof.

(5) Bleach Catalysts. The compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and alpha amino-ketones and mixtures thereof. Suitable alpha amino ketones are for example as described in WO 2012/000846 A1, WO 2008/015443 A1, and WO 2008/014965 A1. Suitable mixtures are as described in USPA 2007/0173430 A1.

In one aspect, the bleach catalyst has a structure corresponding to general formula below:

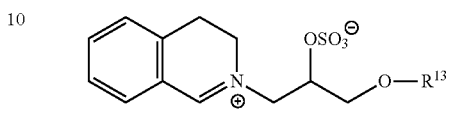

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl;

(6) The composition may preferably comprise catalytic metal complexes. One preferred type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595, 967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

When present, the source of hydrogen peroxide/peracid and/or bleach activator is generally present in the composition in an amount of from about 0.1 to about 60 wt %, from about 0.5 to about 40 wt % or even from about 0.6 to about 10 wt % based on the fabric and home care product. One or more peracids or precursors thereof may be used in combination with one or more hydrophilic peracid or precursor thereof.

Typically hydrogen peroxide source and bleach activator will be incorporated together. The amounts of hydrogen peroxide source and peracid or bleach activator may be selected such that the molar ratio of available oxygen (from the peroxide source) to peracid is from 1:1 to 35:1, or even 2:1 to 10:1.

Surfactant. Preferably the composition comprises a surfactant or surfactant system. The surfactant can be selected from nonionic, anionic, cationic, amphoteric, ampholytic, amphiphilic, zwitterionic, semi-polar nonionic surfactants and mixtures thereof. Preferred compositions comprise a mixture of surfactants/surfactant system. Preferred surfactant systems comprise one or more anionic surfactants, most preferably in combination with a co-surfactant, most preferably a nonionic and/or amphoteric and/or zwitterionic surfactant. Preferred surfactant systems comprise both anionic and nonionic surfactant, preferably in weight ratios from 90:1 to 2:3 or even 1:90. In some instances a weight ratio of anionic to nonionic surfactant of at least 1:1 is preferred. However a ratio below 10:1 may be preferred. When present, the total surfactant level is preferably from 0.1% to 60%, from 1% to 50% or even from 5% to 40% by weight of the subject composition.

Preferably the composition comprises an anionic detersive surfactant, preferably sulphate and/or sulphonate surfactants. Preferred examples include alkyl benzene sulphonates, alkyl sulphates and alkyl alkoxylated sulphates. Preferred sulphonates are $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Preferred sulphate detersive surfactants include alkyl sulphate, typically $C_{8-18}$ alkyl sulphate, or predominantly $C_{12}$ alkyl sulphate. A further preferred alkyl sulphate is alkyl alkoxylated sulphate, preferably a $C_{8-18}$ alkyl alkoxylated sulphate. Preferably the alkoxylating group is an ethoxylating group. Typically the alkyl alkoxylated sulphate has an average degree of alkoxylation of from 0.5 to 30 or 20, or from 0.5 to 10. Particularly preferred are $C_{8-18}$ alkyl ethoxylated sulphate having an average degree of ethoxylation of from 0.5 to 10, from 0.5 to 7, from 0.5 to 5 or even from 0.5 to 3.

The alkyl sulphate, alkyl alkoxylated sulphate and alkyl benzene sulphonates may be linear or branched, substituted or un-substituted. When the surfactant is branched, preferably the surfactant will comprise a mid-chain branched sulphate or sulphonate surfactant. Preferably the branching groups comprise $C_{14}$ alkyl groups, typically methyl and/or ethyl groups.

Preferably the composition comprises a nonionic detersive surfactant. Suitable non-ionic surfactants are selected from the group consisting of: $C_8$-$C_{18}$ alkyl ethoxylates, such as, NEODOL® non-ionic surfactants from Shell; $C_6$-$C_{12}$ alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly (oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, for example a $C_{8-18}$ alkyl ethoxylated alcohol, the alkyl alkoxylated alcohol may have an average degree of alkoxylation of from 1 to 80, preferably from 1 to 50, most preferably from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7, or even below 3 or 2. The alkyl alkoxylated alcohol can be linear or branched, and substituted or un-substituted.

Suitable nonionic surfactants include those with the tradename Lutensol® (BASF).

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

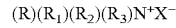

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Suitable amphoteric/zwitterionic surfactants include amine oxides and betaines.

Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, eg, NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Builders. Preferably the composition comprises one or more builders or a builder system. When a builder is used, the composition of the invention will typically comprise at least 1%, or at least 2% to 60% builder. Suitable builders include for example zeolite, phosphate, citrate, etc. It may be preferred that the composition comprises low levels of phosphate salt and/or zeolite, for example from 1 to 10 or 5 wt %. The composition may even be substantially free of strong builder; substantially free of strong builder means "no deliberately added" zeolite and/or phosphate. Typical zeolite builders include zeolite A, zeolite P and zeolite MAP. A typical phosphate builder is sodium tri-polyphosphate.

Chelating Agent. Preferably the composition comprises chelating agents and/or crystal growth inhibitor. Suitable molecules include copper, iron and/or manganese chelating agents and mixtures thereof. Suitable molecules include aminocarboxylates, aminophosphonates, succinates, salts thereof, and mixtures thereof. Non-limiting examples of suitable chelants for use herein include ethylenediaminetetracetates, N-(hydroxyethyl)ethylenediaminetriacetates, nitrilotriacetates, ethylenediamine tetraprorionates, triethylenetetraaminehexacetates, diethylenetriamine-pentaacetates, ethanoldiglycines, ethylenediaminetetrakis (methylenephosphonates), diethylenetriamine penta(methylene phosphonic acid) (DTPMP), ethylenediamine disuccinate (EDDS), hydroxyethanedimethylenephosphonic acid (HEDP), methylglycinediacetic acid (MGDA), diethylenetriaminepentaacetic acid (DTPA), salts thereof, and mixtures thereof. Other nonlimiting examples of chelants of use in the present invention are found in U.S. Pat. Nos. 7,445,644, 7,585,376 and 2009/0176684A1. Other suitable chelating agents for use herein are the commercial DEQUEST series, and chelants from Monsanto, DuPont, and Nalco, Inc.

pH Modifiers. pH modifiers may be incorporated to generate the desired pH. Any alkali or acid may be added known to those skilled in the art of detergent manufacture, for example, sodium or potassium hydroxide carbonate or silicate, citric acid, or stronger acids such as hydrochloric acid. Those pH modifiers which add buffering capacity may be particularly preferred.

Silicate Salts. The composition may preferably also contain silicate salts, such as sodium or potassium silicate. The composition may comprise from 0 wt % to less than 10 wt % silicate salt, to 9 wt %, or to 8 wt %, or to 7 wt %, or to 6 wt %, or to 5 wt %, or to 4 wt %, or to 3 wt %, or even to 2 wt %, and preferably from above 0 wt %, or from 0.5 wt %, or even from 1 wt % silicate salt. A suitable silicate salt is sodium silicate.

Dispersants. The composition may preferably also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilisers. The composition may preferably comprise enzyme stabilizers. Any conventional enzyme stabilizer may be used, for example by the presence of water-soluble sources of calcium and/or magnesium ions in the finished fabric and home care products that provide such ions to the enzymes. In case of aqueous compositions comprising protease, a reversible protease inhibitor, such as a boron compound including borate, or preferably 4-formyl phenylboronic acid, phenylboronic acid and derivatives thereof, or compounds such as calcium formate, sodium formate and 1,2-propane diol, diethylene glycol can be added to further improve stability.

Fabric Shading Dye. The composition may comprise fabric shading dye. Suitable fabric shading dye (sometimes referred to as hueing, bluing or whitening agents) typically provides a blue or violet shade to fabric. Fabric shading dyes can be used either alone or in combination to create a specific shade of hueing and/or to shade different fabric types. This may be provided for example by mixing a red and green-blue dye to yield a blue or violet shade. The fabric shading dye may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric shading dyes include dyes and dye-clay conjugates. Preferred fabric shading dyes are selected from small molecule dyes and polymeric dyes. Suitable small molecule dyes include small molecule dyes selected from the group consisting of dyes falling into the Colour Index (C.I.) classifications of Acid, Direct, Basic, Reactive, Solvent or Disperse dyes for example that are classified as Blue, Violet, Red, Green or Black, and provide the desired shade either alone or in combination with other dyes or in combination with other adjunct ingredients. Dyes described as hydrolysed Reactive dyes, as described in EP-A-1794274 may also be included. In another aspect, suitable small molecule dyes include small molecule dyes selected from the group consisting of Colour Index (Society of Dyers and Colourists, Bradford, UK) numbers Direct Violet dyes such as 5, 7, 9, 11, 31, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 48, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes such as those described in US 2008/034511 A1 or U.S. Pat. No. 8,268,016 B2, or dyes as disclosed in U.S. Pat. No. 7,208,459 B2, such as solvent violet 13 and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in WO2011/98355, US 2012/225803 A1, US 2012/090102 A1, WO2012/166768, U.S. Pat. No. 7,686,892 B2, and WO2010/142503.

Other suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet Conn., carboxymethyl cellulose (CMC) covalently bound to one or more reactive blue, reactive violet or reactive red dye such as CMC conjugated with C.I. Reactive Blue 19, sold by Megazyme, Wicklow, Ireland under the product name AZO-CM-CEL- LULOSE, product code S-ACMC, alkoxylated triphenyl-methane polymeric colourants, alkoxylated thiophene polymeric colourants, alkoxylated carbocyclic and alkoxylated heterocyclic azo colourants, and mixtures thereof. Preferred polymeric dyes comprise the optionally substituted alkoxylated dyes, such as alkoxylated triphenyl-methane polymeric colourants, alkoxylated thiophene polymeric colourants, alkoxylated carbocyclic and alkoxylated heterocyclic azo colourants, and mixtures thereof, such as the Liquitint dyes.

Preferred hueing dyes include the whitening agents found in WO 08/87497 A1, WO2011/011799 and US 2012/129752 A1. Preferred hueing agents for use in the present invention may be the preferred dyes disclosed in these references, including those selected from Examples 1-42 in Table 5 of WO2011/011799. Other preferred dyes are disclosed in U.S. Pat. No. 8,138,222. Other preferred dyes are disclosed in U.S. Pat. No. 7,909,890 B2.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye and a clay selected from the group consisting of Montmorillonite clay, Hectorite clay, Saponite clay and mixtures thereof. Examples of suitable cationic/basic dyes include C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The fabric shading dye or indeed other adjuncts made by organic synthesis routes such as pigment, optical brightener, polymer may be incorporated into the detergent composition as part of a reaction mixture which is the result of the organic synthesis for the adjunct with optional purification step(s). Such reaction mixtures generally comprise the adjunct itself and in addition may comprise un-reacted starting materials and/or by-products of the organic synthesis route.

Suitable polymeric fabric shading dyes are illustrated below. As with all such alkoxylated compounds, the organic synthesis may produce a mixture of molecules having different degrees of alkoxylation. Such mixtures may be used directly to provide the fabric shading dye, or may undergo a purification step.

The fabric shading dye may have the following structure:

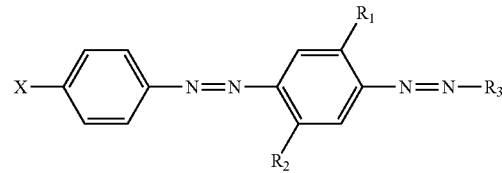

wherein:
$R_1$ and $R_2$ are independently selected from the group consisting of: H; alkyl; alkoxy;
alkyleneoxy; alkyl capped alkyleneoxy; urea; and amido;
$R_3$ is a substituted aryl group;
X is a substituted group comprising sulfonamide moiety and optionally an alkyl and/or aryl moiety, and wherein the substituent group comprises at least one alkyleneoxy chain. The hueing dye may be a thiophene dye such as a thiophene azo dye, preferably alkoxylated. Optionally the dye may be substituted with at least one solubilising group selected from sulphonic, carboxylic or quaternary ammonium groups.
Examples of suitable fabric shading dyes are:

Dye Formula 1

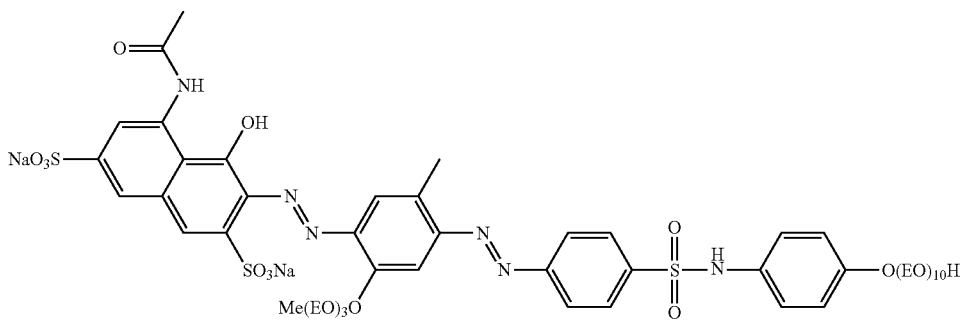

Dye Formula 2

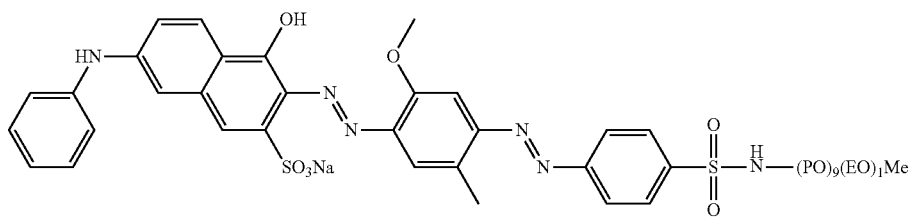

-continued
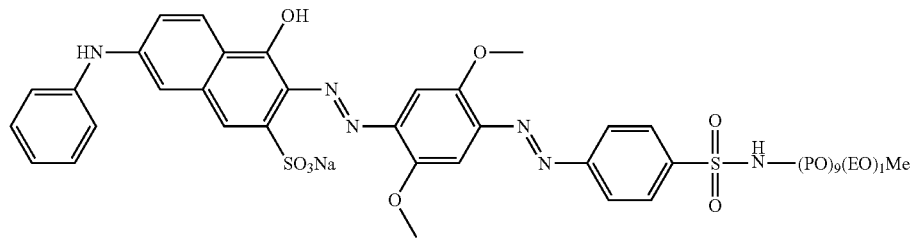
Dye Formula 3
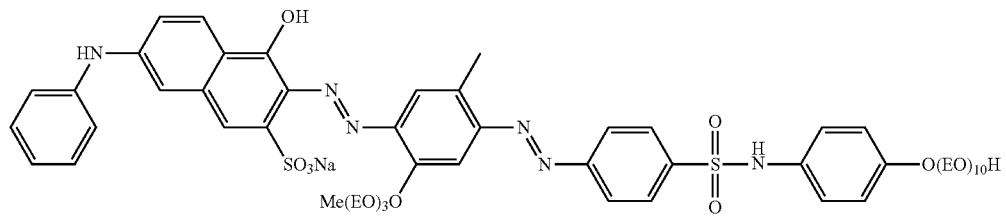
Dye Formula 4
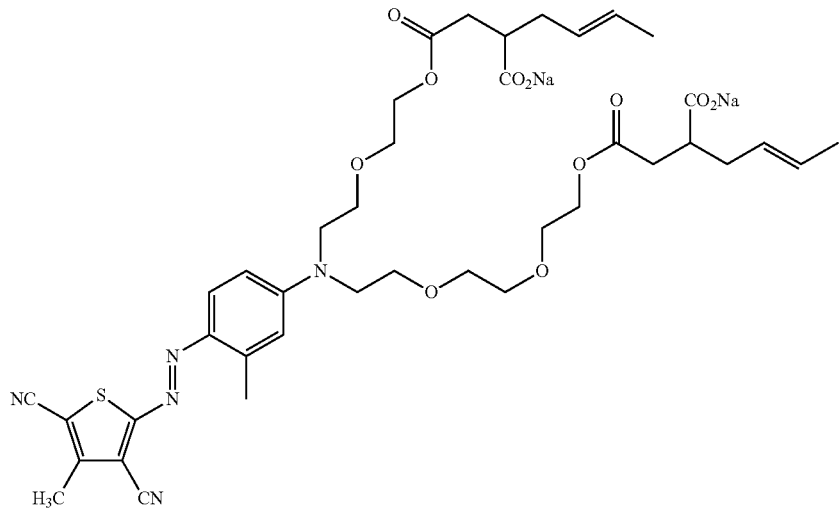
Dye Formula 5
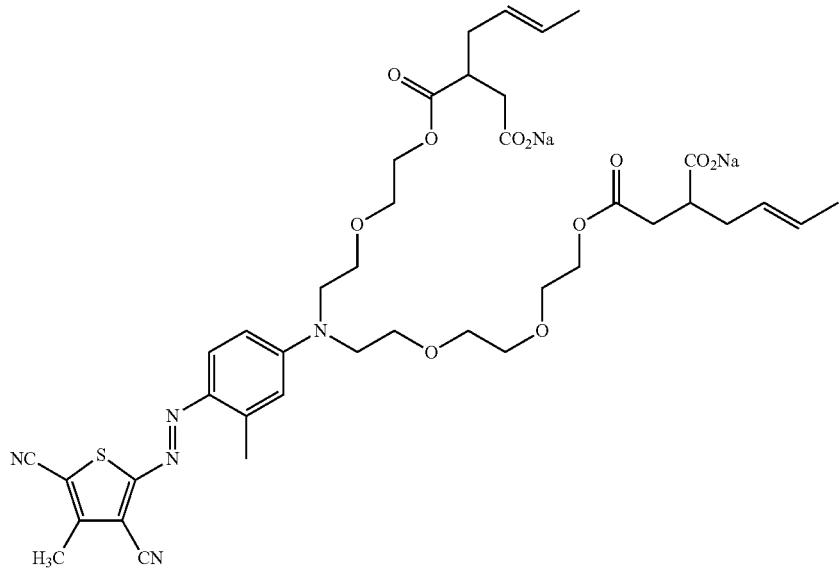
Dye Formula 6

-continued

Dye Formula 7

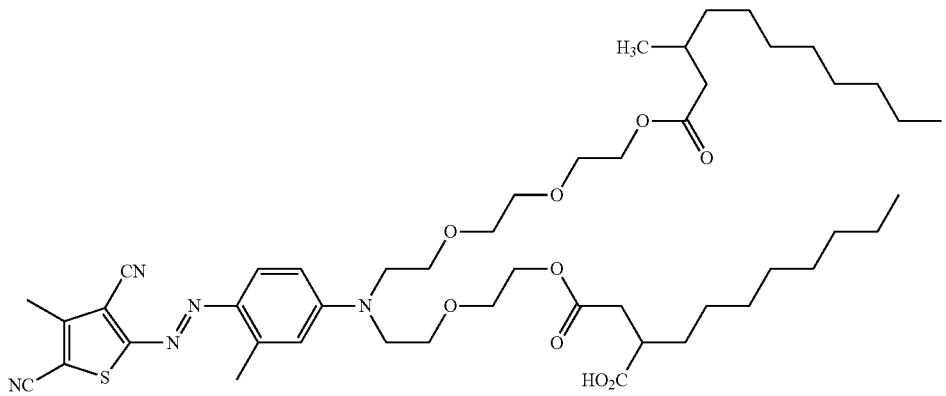

Dye Formula 8

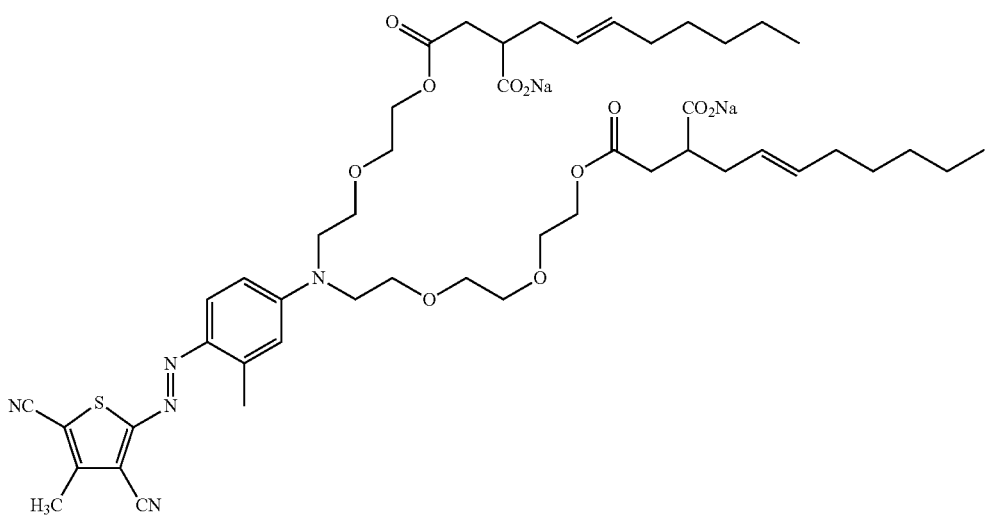

The dye may comprise
a) a Zn—, Ca—, Mg—, Na—, K—, Al, Si—, Ti—, Ge—, Ga—, Zr—, In— or Sn— phthalocyanine compound of formula (1)

(PC)-L-(D)     (1)

to which at least one mono-azo dyestuff is attached through a covalent bonding via a linking group L wherein
PC is a metal-containing phthalocyanine ring system;
D is the radical of a mono-azo dyestuff; and
L is a group

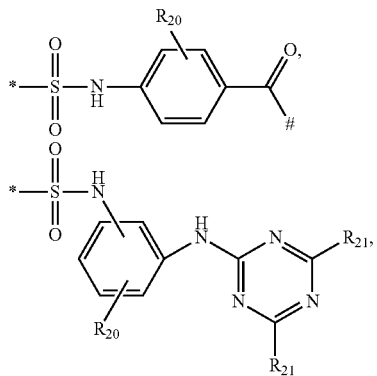

-continued

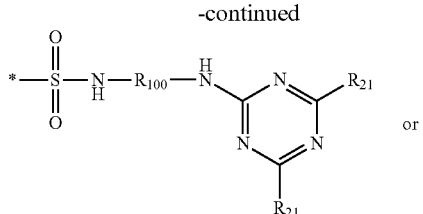

or

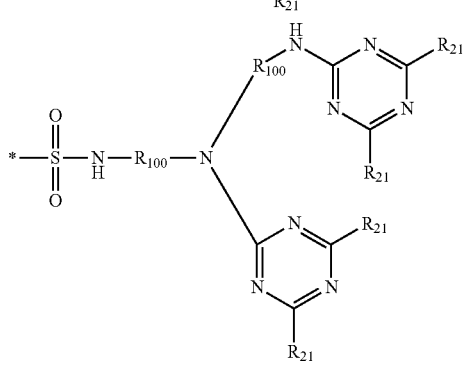

wherein
$R_{20}$ is hydrogen, $C_1$-$C_8$alkyl, $C_1$-$C_8$alkoxy or halogen;
$R_{21}$ is independently D, hydrogen, OH, Cl or F, with the proviso that at least one is D;

R$_{100}$ is C$_1$-C$_8$alkylene

* is the point of attachment of PC;
# is the point of attachment of the dye.

The aforementioned fabric shading dyes can be used in combination (any mixture of fabric hueing agents can be used).

Pigments. Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. Other suitable pigments are described in WO2008/090091. In another aspect, suitable pigments include pigments selected from the group consisting of Ultramarine Blue (C.I. Pigment Blue 29), Ultramarine Violet (C.I. Pigment Violet 15), Monastral Blue and mixtures thereof. Particularly preferred are Pigment Blues 15 to 20, especially Pigment Blue 15 and/or 16. Other suitable pigments include those selected from the group consisting of Ultramarine Blue (C.I. Pigment Blue 29), Ultramarine Violet (C.I. Pigment Violet 15), Monastral Blue and mixtures thereof. Suitable hueing agents are described in more detail in U.S. Pat. No. 7,208,459 B2.

azoles, 5- and 6-membered-ring heterocycles, and other miscellaneous agents. Particularly preferred brighteners are selected from: sodium 2 (4-styryl-3-sulfophenyl)-2H-naphtho [1,2-d] triazole, disodium 4,4'-bis([4-anilino-6-(N-methyl-2-hydroxyethylamino)-1,3,5-triazin-2-yl]amino)stilbene-2,2'-disulfonate, disodium 4,4'-bis[(4-anilino-6-morpholino-1,3,5-triazin-2-yl)amino]stilbene-2,2'-disulfonate, and disodium 4,4'-bis(2-sulfostyryl)biphenyl. Other examples of such brighteners are disclosed in "The Production and Application of Fluorescent Brightening Agents", M. Zahradnik, Published by John Wiley & Sons, New York (1982).

A preferred brightener has the structure below:

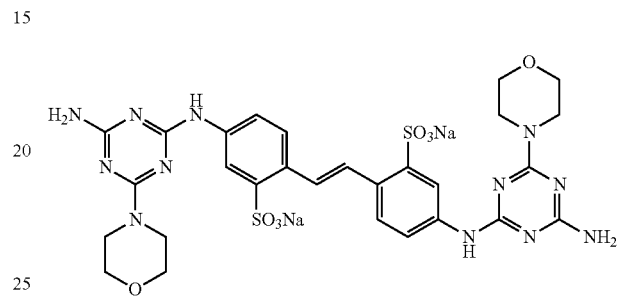

Suitable levels of brightener are from about 0.01, from about 0.05, from about 0.1 or even from about 0.2 wt % to upper levels of 0.5, of 0.75 or even 1.0 wt %.

A highly preferred optical brightener comprises C.I. fluorescent brightener 260 (preferably having the following structure:

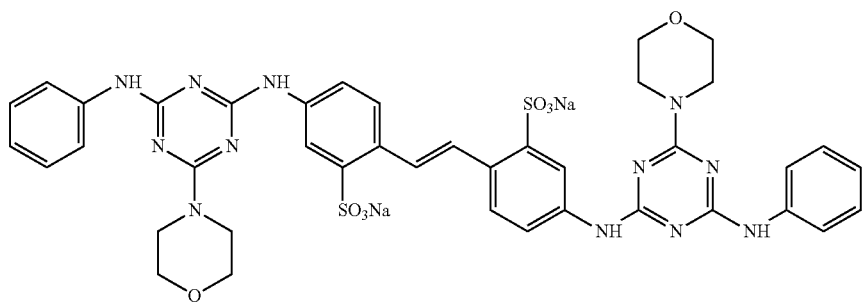

The aforementioned fabric hueing agents can be used in mixtures of hueing agents and/or in mixtures with any pigment.

Optical Brighteners. The benefit agent may comprise one or more optical brighteners. Suitable examples of optical brighteners are for example stilbene brighteners, coumarinic brighteners, benzoxazole brighteners and mixtures thereof. Diaminostilbene disulphonic acid type brighteners (hereinafter referred to as "DAS") are classified as hydrophilic in WO-A-98/52907. A commercial example of a DAS is Tinopal DMS (ex CIBA). Another type of low ClogP brightener is a distyrylbiphenyl brightener (hereinafter referred to as "DSBP"). A commercial example of this type of brightener is Tinopal CBS-X (also ex CIBA). Commercial optical brighteners which may be useful in the present invention can be classified into subgroups, which include, but are not limited to, derivatives of stilbene, pyrazoline, carboxylic acid, methinecyanines, dibenzothiophene-5,5-dioxide, A process for making C.I fluorescent brightener 260 is described in BE680847.

Aesthetic Dyes. The composition may comprise aesthetic dyes and/or pigments. Suitable dyes include any conventional dye, typically small molecule or polymeric, used for colouring cleaning and/or treatment compositions. These are generally non-fabric shading dyes.

Solvent System. The present compositions may comprise a solvent system for example comprising water alone or mixtures of organic solvents either without or with water. Preferred organic solvents include 1,2-propanediol, ethanol, glycerol, dipropylene glycol, methyl propane diol and mixtures thereof. Other lower alcohols, C1-C4 alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 1% to about 50%, more usually from about 5% to about 25%. Such solvent systems may be particularly useful for pre-mixing with the brightener prior to mixing the brightener with other components in the detergent composition. Alternatively or in addition, surfactant(s) may be pre-mixed with the brightener. In such a preferred embodiment, the surfactant pre-mixed with the brightener comprises at least 25 wt % or at least 50 wt % (based on the total weight of the surfactant) of nonionic surfactant.

In some embodiments of the invention, the composition is in the form of a structured liquid. Such structured liquids can either be internally structured, whereby the structure is formed by primary ingredients (e.g. surfactant material) and/or externally structured by providing a three dimensional matrix structure using secondary ingredients (e.g. polymers, clay and/or silicate material), for use e.g. as thickeners. The composition may comprise a structurant, preferably from 0.01 wt % to 5 wt %, from 0.1 wt % to 2.0 wt % structurant. Examples of suitable structurants are given in US2006/0205631A1, US2005/0203213A1, U.S. Pat. Nos. 7,294,611, 6,855,680. The structurant is typically selected from the group consisting of diglycerides and triglycerides, ethylene glycol distearate, microcrystalline cellulose, cellulose-based materials, microfiber cellulose, ally modified alkali-swellable emulsions such as Polygel W30 (3VSigma), biopolymers, xanthan gum, gellan gum, hydrogenated castor oil, derivatives of hydrogenated castor oil such as non-ethoxylated derivatieves thereof and mixtures thereof, in particular, those selected from the group of hydrogenated castor oil, derivatives of hydrogenated castor oil, microfibullar cellulose, hydroxyfunctional crystalline materials, long chain fatty alcohols, 12-hydroxystearic acids, clays and mixtures thereof. A preferred structurant is described in. U.S. Pat. No. 6,855,680 which defines suitable hydroxyfunctional crystalline materials in detail. Preferred is hydrogenated castor oil. Non-limiting examples of useful structurants include. Such structurants have a thread-like structuring system having a range of aspect ratios. Other suitable structurants and the processes for making them are described in WO2010/034736.

The composition of the present invention may comprise a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992. When present, the high melting point fatty compound is preferably included in the composition at a level of from 0.1% to 40%, preferably from 1% to 30%, more preferably from 1.5% to 16% by weight of the composition, from 1.5% to 8% in view of providing improved conditioning benefits such as slippery feel during the application to wet hair, softness and moisturized feel on dry hair.

Cationic Polymer. The compositions of the present invention may contain a cationic polymer. Concentrations of the cationic polymer in the composition typically range from 0.05% to 3%, in another embodiment from 0.075% to 2.0%, and in yet another embodiment from 0.1% to 1.0%. Suitable cationic polymers will have cationic charge densities of at least 0.5 meq/gm, in another embodiment at least 0.9 meq/gm, in another embodiment at least 1.2 meq/gm, in yet another embodiment at least 1.5 meq/gm, but in one embodiment also less than 7 meq/gm, and in another embodiment less than 5 meq/gm, at the pH of intended use of the composition, which pH will generally range from pH 3 to pH 9, in one embodiment between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, in one embodiment between 50,000 and 5 million, and in another embodiment between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1.

Nonionic Polymer. The composition of the present invention may include a nonionic polymer as a conditioning agent. Polyalkylene glycols having a molecular weight of more than 1000 are useful herein. Useful are those having the following general formula:

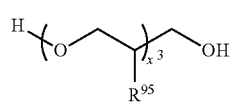

wherein R95 is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from about 0.01% to about 10%. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US Patent Application Nos. 2007/0286837A1; 2005/0048549A1; 2007/0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

Dye Transfer Inhibitor (DTI). The cleaning and/or treatment compositions preferably comprise one or mixtures of more than one dye transfer inhibiting agents. Suitable dye transfer inhibitors are selected from the group consisting of: polyvinylpyrrolidone polymers, polyamine N-oxide polymers, copolymers of N-vinylpyrrolidone and N-vinylimidazole, polyvinyloxazolidones, polyvinylimidazoles and mixtures thereof. Other suitable DTIs are triazines as described in WO2012/095354, polymerized benzoxazines as described in WO2010/130624, polyvinyl tetrazoles as described in DE 102009001144A, porous polyamide particles as described in WO2009/127587 and insoluble polymer particles as described in WO2009/124908. Other suitable DTIs are described in WO2012/004134, or polymers selected from the group consisting of (a) amphiphilic alkoxylated polyamines, amphiphilic graft co-polymers, zwitterionic soil suspension polymers, manganese phthalocyanines, peroxidases and mixtures thereof.

Preferred classes of DTI include but are not limited to polyvinylpyrrolidone polymers, polyamine N-oxide polymers, copolymers of N-vinylpyrrolidone and N-vinylimidazole, polyvinyloxazolidones, polyvinylimidazoles and mixtures thereof. More specifically, the polyamine N-oxide polymers preferred for use herein contain units having the following structural formula: R-AX-P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

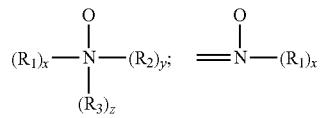

wherein R1, R2, R3 are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa<10, preferably pKa<7, more preferred pKa<6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization.

Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., Chemical Analysis, Vol 113. "Modem Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1.

These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference.

Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

A mixed polymer system comprising copolymers of (a) N-vinylpyrrolidone and N-vinylimidazole and (b) polyamine N-oxide polymers, particularly poly 4-vinylpyridine N-oxide are a particularly preferred DTI system, particularly preferred in weight ratios of (a):(b) of 5:1 to 1:5. Preferred molecular weights for the DTI essential to the present invention are from 1000 to 250000 Daltons, more preferably from 2000 to 150000 or even from 8000 to 100000 Daltons.

Suitable examples include PVP-K15, PVP-K30, ChromaBond S-400, ChromaBond S-403E and Chromabond S-100 from Ashland Aqualon, and Sokalan® HP165, Sokalan® HP50, Sokalan® HP53, Sokalan® HP59, Sokalan® HP 56K, Sokalan® HP 66 from BASF.

The inventors have found that the compositions comprising optical brightener and DTI provide significant increase in whiteness and this is surprising because typically DTIs reduce the efficacy of optical brighteners.

The dye transfer inhibiting agent may be present at levels from about 0.0001% to about 15%, from about 0.01% to about 10%, preferably from about 0.01% to about 5% by weight of the composition.

Organic Conditioning Oil. The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

Hygiene Agent. The compositions of the present invention may also comprise components to deliver hygiene and/or malodour benefits such as one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag+ or nano-silver dispersions.

Probiotics. The composition may comprise probiotics, such as those described in WO2009/043709.

Suds Boosters. The composition may preferably comprise suds boosters if high sudsing is desired. Suitable examples are the C10-C16 alkanolamides or C10-C14 alkyl sulphates, which are preferably incorporated at 1%-10% levels. The C10-C14 monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as MgCl2, MgSO4, CaCl2, CaSO4 and the like, can be added at levels of, typically, 0.1%-2%, to provide additional suds and to enhance grease removal performance.

Suds Supressor. Compounds for reducing or suppressing the formation of suds may be incorporated into the compositions of the present invention. Suds suppression can be of particular importance in the so-called "high concentration cleaning process" as described in U.S. Pat. Nos. 4,489,455 and 4,489,574, and in front-loading-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic C18-C40 ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265, 779; 4,265,779; 3,455,839; 3,933,672; 4,652,392; 4,978, 471; 4,983,316; 5,288,431; 4,639,489; 4,749,740; and U.S. Pat. Nos. 4,798,679; 4,075,118; European Patent Application No. 89307851.9; EP 150,872; and DOS 2,124,526.

For any detergent compositions to be used in automatic laundry washing machines, suds should not form to the extent that they overflow the washing machine. Suds suppressors, when utilized, are preferably present in a "suds suppressing amount". By "suds suppressing amount" is meant that the formulator of the composition can select an amount of this suds controlling agent that will sufficiently control the suds to result in a low-sudsing laundry detergent for use in automatic laundry washing machines. The compositions herein will generally comprise from 0% to 10% of suds suppressor. When utilized as suds suppressors, monocarboxylic fatty acids, and salts therein, will be present typically in amounts up to 5%, by weight, of the detergent composition. Preferably, from 0.5% to 3% of fatty monocarboxylate suds suppressor is utilized. Silicone suds suppressors are typically utilized in amounts up to 2.0%, by weight, of the detergent composition, although higher amounts may be used. Monostearyl phosphate suds suppressors are generally utilized in amounts ranging from 0.1% to 2%, by weight, of the composition. Hydrocarbon suds suppressors are typically utilized in amounts ranging from 0.01% to 5.0%, although higher levels can be used. The alcohol suds suppressors are typically used at 0.2%-3% by weight of the finished compositions.

Pearlescent Agents. Pearlescent agents as described in WO2011/163457 may be incorporated into the compositions of the invention.

Perfume. Preferably the composition comprises a perfume, preferably in the range from 0.001 to 3 wt %, most preferably from 0.1 to 1 wt %. Many suitable examples of perfumes are provided in the CTFA (Cosmetic, Toiletry and Fragrance Association) 1992 International Buyers Guide, published by CFTA Publications and OPD 1993 Chemicals Buyers Directory 80$^{th}$ Annual Edition, published by Schnell Publishing Co. It is usual for a plurality of perfume components to be present in the compositions of the invention, for example four, five, six, seven or more. In perfume mixtures preferably 15 to 25 wt % are top notes. Top notes are defined by Poucher (Journal of the Society of Cosmetic Chemists 6(2):80 [1995]). Preferred top notes include rose oxide, citrus oils, linalyl acetate, lavender, linalool, dihydromyrcenol and cis-3-hexanol.

Packaging. Any conventional packaging may be used and the packaging may be fully or partially transparent so that he consumer can see the colour of the product which may be provided or contributed to by the colour of the dyes essential to the invention. UV absorbing compounds may be included in some or all of the packaging.

Process of Making Compositions

The compositions of the invention may be solid (for example granules or tablets) or liquid form. Preferably the compositions are in liquid form. They may be made by any process chosen by the formulator, non-limiting examples of which are described in the examples and in U.S. Pat. No. 4,990,280; U.S. 20030087791A1; U.S. 20030087790A1; U.S. 20050003983A1; U.S. 20040048764A1; U.S. Pat. Nos. 4,762,636; 6,291,412; U.S. 20050227891A1; EP 1070115A2; U.S. Pat. Nos. 5,879,584; 5,691,297; 5,574,005; 5,569,645; 5,565,422; 5,516,448; 5,489,392; U.S. 5,486.

When in the form of a liquid, the compositions of the invention may be aqueous (typically above 2 wt % or even above 5 or 10 wt % total water, up to 90 or up to 80 wt % or 70 wt % total water) or non-aqueous (typically below 2 wt % total water content). Typically the compositions of the invention will be in the form of an aqueous solution or uniform dispersion or suspension of optical brightener, DTI and optional additional adjunct materials, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable. When in the form of a liquid, the detergents of the invention preferably have viscosity from 1 to 1500 centipoises (1-1500 mPa*s), more preferably from 100 to 1000 centipoises (100-1000 mPa*s), and most preferably from 200 to 500 centipoises (200-500 mPa*s) at 20 s−1 and 21° C. Viscosity can be determined by conventional methods. Viscosity may be measured using an AR 550 rheometer from TA instruments using a plate steel spindle at 40 mm diameter and a gap size of 500 μm. The high shear viscosity at 20 s−1 and low shear viscosity at 0.05-1 can be obtained from a logarithmic shear rate sweep from 0.1-1 to 25-1 in 3 minutes time at 21C. The preferred rheology described therein may be achieved using internal existing structuring with detergent ingredients or by employing an external rheology modifier. More preferably the detergents, such as detergent liquid compositions have a high shear rate viscosity of from about 100 centipoise to 1500 centipoise, more preferably from 100 to 1000 cps. Unit Dose detergents, such as detergent liquid compositions have high shear rate viscosity of from 400 to 1000cps. Detergents such as laundry softening compositions typically have high shear rate viscosity of from 10 to 1000, more preferably from 10 to 800 cps, most preferably from 10 to 500 cps. Hand dishwashing compositions have high shear rate viscosity of from 300 to 4000 cps, more preferably 300 to 1000 cps.

The cleaning and/or treatment compositions in the form of a liquid herein can be prepared by combining the components thereof in any convenient order and by mixing, e.g., agitating, the resulting component combination to form a phase stable liquid detergent composition. In a process for preparing such compositions, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes. Preferably the benefit agent delivery system will be added in a second low shear mixing step, after the higher shear mixing of the majority of the ingredients in the liquid.

Pouches. In a preferred embodiment of the invention, the composition is provided in the form of a unitized dose, either tablet form or preferably in the form of a liquid/solid (optionally granules)/gel/paste held within a water-soluble film in what is known as a pouch or pod. The composition can be encapsulated in a single or multi-compartment pouch. Multi-compartment pouches are described in more detail in EP-A-2133410. When the composition is present in a multi-compartment pouch, the benefit agent delivery system may be in one or two or more compartments. Shading or non-shading dyes or pigments or other aesthetics may also be used in one or more compartments. In one embodiment the benefit agent delivery system is present in a single compartment of a multi-compartment pouch.

Suitable film for forming the pouches is soluble or dispersible in water, and preferably has a water-solubility/dispersibility of at least 50%, preferably at least 75% or even at least 95%, as measured by the method set out here after using a glass-filter with a maximum pore size of 20 microns:

50 grams±0.1 gram of pouch material is added in a pre-weighed 400 ml beaker and 245 ml±1 ml of distilled water is added. This is stirred vigorously on a magnetic stirrer set at 600 rpm, for 30 minutes. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated. Preferred film materials are polymeric materials. The film material can be obtained, for example, by casting, blow-moulding, extrusion or blown extrusion of the polymeric material, as known in the art. Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol. Preferred for use herein are polymers which are from about 60% to about 98% hydrolysed, preferably about 80% to about 90% hydrolysed, to improve the dissolution characteristics of the material.

Naturally, different film material and/or films of different thickness may be employed in making the compartments of the present invention. A benefit in selecting different films is that the resulting compartments may exhibit different solubility or release characteristics.

Most preferred film materials are PVA films known under the MonoSol trade reference M8630, M8900, H8779 (as described in the Applicants co-pending applications ref 44528 and 11599) and those described in U.S. Pat. Nos. 6,166,117 and 6,787,512 and PVA films of corresponding solubility and deformability characteristics.

The film material herein can also comprise one or more additive ingredients. For example, it can be beneficial to add plasticisers, for example glycerol, ethylene glycol, diethyleneglycol, propylene glycol, sorbitol and mixtures thereof. Other additives include functional detergent additives to be delivered to the wash water, for example organic polymeric dispersants, etc.

Bittering agent may be incorporated into a pouch or pod, either by incorporation in the composition inside the pouch, and/or by coating onto the film.

Process for Making the Water-Soluble Pouch

The compositions of the invention in pouch form may be made using any suitable equipment and method. However the multi-compartment pouches are preferably made using the horizontal form filling process. The film is preferably wetting, more preferably heated to increase the malleability thereof. Even more preferably, the method also involves the use of a vacuum to draw the film into a suitable mould. The vacuum drawing the film into the mould can be applied for 0.2 to 5 seconds, preferably 0.3 to 3 or even more preferably 0.5 to 1.5 seconds, once the film is on the horizontal portion of the surface. This vacuum may preferably be such that it provides an under-pressure of between −100 mbar to −1000 mbar, or even from −200 mbar to −600 mbar.

The moulds, in which the pouches are made, can have any shape, length, width and depth, depending on the required dimensions of the pouches. The moulds can also vary in size and shape from one to another, if desirable. For example, it may be preferred that the volume of the final pouches is between 5 and 300 ml, or even 10 and 150 ml or even 20 and 100 ml and that the mould sizes are adjusted accordingly.

Heat can be applied to the film, in the process commonly known as thermoforming, by any means. For example the film may be heated directly by passing it under a heating element or through hot air, prior to feeding it onto the surface or once on the surface. Alternatively it may be heated indirectly, for example by heating the surface or applying a hot item onto the film. Most preferably the film is heated using an infra red light. The film is preferably heated to a temperature of 50 to 120° C., or even 60 to 90° C. Alternatively, the film can be wetted by any mean, for example directly by spraying a wetting agent (including water, solutions of the film material or plasticizers for the film material) onto the film, prior to feeding it onto the surface or once on the surface, or indirectly by wetting the surface or by applying a wet item onto the film.

In the case of pouches comprising powders it is advantageous to pin prick the film for a number of reasons: (a) to reduce the possibility of film defects during the pouch formation, for example film defects giving rise to rupture of the film can be generated if the stretching of the film is too fast; (b) to permit the release of any gases derived from the product enclosed in the pouch, as for example oxygen formation in the case of powders containing bleach; and/or (c) to allow the continuous release of perfume. Moreover, when heat and/or wetting is used, pin pricking can be used before, during or after the use of the vacuum, preferably during or before application of the vacuum. Preferred is thus that each mould comprises one or more holes which are connected to a system which can provide a vacuum through these holes, onto the film adjacent the holes.

Once a film has been heated/wetted, it is drawn into an appropriate mould, preferably using a vacuum. The filling of the moulded film can be done by any known method for filling (moving) items. The most preferred method will depend on the product form and speed of filling required. Preferably the moulded film is filled by in-line filling techniques. The filled, open pouches are then closed, using a second film, by any suitable method. Preferably, this is also done while in horizontal position and in continuous, constant motion. Preferably the closing is done by continuously feeding a second material or film, preferably water-soluble film, over and onto the web of open pouches and then preferably sealing the first film and second film together, typically in the area between the moulds and thus between the pouches.

Preferred methods of sealing include heat sealing, solvent welding, and solvent or wet sealing. It is preferred that only the area which is to form the seal, is treated with heat or solvent. The heat or solvent can be applied by any method, preferably on the closing material, preferably only on the areas which are to form the seal. If solvent or wet sealing or welding is used, it may be preferred that heat is also applied. Preferred wet or solvent sealing/welding methods include applying selectively solvent onto the area between the moulds, or on the closing material, by for example, spraying or printing this onto these areas, and then applying pressure onto these areas, to form the seal. Sealing rolls and belts as described above (optionally also providing heat) can be used, for example.

The formed pouches can then be cut by a cutting device. Cutting can be done using any known method. It may be preferred that the cutting is also done in continuous manner, and preferably with constant speed and preferably while in horizontal position. The cutting device can, for example, be a sharp item or a hot item, whereby in the latter case, the hot item 'burns' through the film/sealing area.

The different compartments of a multi-compartment pouch may be made together in a side-by-side style and consecutive pouches are not cut. Alternatively, the compartments can be made separately. According to this process and preferred arrangement, the pouches are made according to the process comprising the steps of:

a) forming an first compartment (as described above);
b) forming a recess within some or all of the closed compartment formed in step (a), to generate a second moulded compartment superposed above the first compartment;
c) filling and closing the second compartments by means of a third film;
d) sealing said first, second and third films; and
e) cutting the films to produce a multi-compartment pouch.

Said recess formed in step b is preferably achieved by applying a vacuum to the compartment prepared in step a).

Alternatively the second, and optionally third, compartment(s) can be made in a separate step and then combined with the first compartment as described in our co-pending application EP 08101442.5 which is incorporated herein by reference. A particularly preferred process comprises the steps of:

a) forming a first compartment, optionally using heat and/or vacuum, using a first film on a first forming machine;
b) filling said first compartment with a first composition;
c) on a second forming machine, deforming a second film, optionally using heat and vacuum, to make a second and optionally third moulded compartment;
d) filling the second and optionally third compartments;
e) sealing the second and optionally third compartment using a third film;
f) placing the sealed second and optionally third compartments onto the first compartment;
g) sealing the first, second and optionally third compartments; and
h) cutting the films to produce a multi-compartment pouch The first and second forming machines are selected based on their suitability to perform the above process. The first forming machine is preferably a horizontal forming machine. The second forming machine is preferably a rotary drum forming machine, preferably located above the first forming machine.

It will be understood moreover that by the use of appropriate feed stations, it is possible to manufacture multi-compartment pouches incorporating a number of different or distinctive compositions and/or different or distinctive liquid, gel or paste compositions.

Method of Use. The compositions of this invention, typically prepared as hereinbefore described, can be used to form aqueous washing/treatment solutions for use in the laundering/treatment of fabrics. Generally, an effective amount of such a composition is added to water, for example in a conventional fabric automatic washing machine, to form such aqueous laundering solutions. The aqueous washing solution so formed is then contacted, typically under agitation, with the fabrics to be laundered/treated therewith. An effective amount of the detergent composition herein added to water to form aqueous laundering solutions can comprise amounts sufficient to form from about 500 to 25,000 ppm, or from 500 to 15,000 ppm of composition in aqueous washing solution, or from about 1,000 to 3,000 ppm of the detergent compositions herein will be provided in aqueous washing solution.

Typically, the wash liquor is formed by contacting the detergent with wash water in such an amount so that the concentration of the detergent in the wash liquor is from above 0 g/l to 5 g/l, or from 1 g/l, and to 4.5 g/l, or to 4.0 g/l, or to 3.5 g/l, or to 3.0 g/l, or to 2.5 g/l, or even to 2.0 g/l, or even to 1.5 g/l. The method of laundering fabric or textile may be carried out in a top-loading or front-loading automatic washing machine, or can be used in a hand-wash laundry application. In these applications, the wash liquor formed and concentration of laundry detergent composition in the wash liquor is that of the main wash cycle. Any input of water during any optional rinsing step(s) is not included when determining the volume of the wash liquor.

The wash liquor may comprise 40 litres or less of water, or 30 litres or less, or 20 litres or less, or 10 litres or less, or 8 litres or less, or even 6 litres or less of water. The wash liquor may comprise from above 0 to 15 litres, or from 2 litres, and to 12 litres, or even to 8 litres of water. Typically from 0.01 kg to 2 kg of fabric per litre of wash liquor is dosed into said wash liquor. Typically from 0.01 kg, or from 0.05 kg, or from 0.07 kg, or from 0.10 kg, or from 0.15 kg, or from 0.20 kg, or from 0.25 kg fabric per litre of wash liquor is dosed into said wash liquor. Optionally, 50 g or less, or 45 g or less, or 40 g or less, or 35 g or less, or 30 g or less, or 25 g or less, or 20 g or less, or even 15 g or less, or even 10 g or less of the composition is contacted to water to form the wash liquor. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1. Typically the wash liquor comprising the detergent of the invention has a pH of from 3 to 11.5.

In one aspect, such method comprises the steps of optionally washing and/or rinsing said surface or fabric, contacting said surface or fabric with any composition disclosed in this specification then optionally washing and/or rinsing said surface or fabric is disclosed, with an optional drying step.

Drying of such surfaces or fabrics may be accomplished by any one of the common means employed either in domestic or industrial settings: machine drying or open-air drying. The fabric may comprise any fabric capable of being laundered in normal consumer or institutional use conditions, and the invention is particularly suitable for synthetic textiles such as polyester and nylon and especially for treatment of mixed fabrics and/or fibres comprising synthetic and cellulosic fabrics and/or fibres. As examples of synthetic fabrics are polyester, nylon, these may be present in mixtures with cellulosic fibres, for example, polycotton fabrics. The solution typically has a pH of from 7 to 11, more usually 8 to 10.5. The compositions are typically employed at concentrations from 500 ppm to 5,000 ppm in solution. The water temperatures typically range from about 5° C. to about 90° C. The water to fabric ratio is typically from about 1:1 to about 30:1.

The benefit agent delivery system and adjunct ingredients in the compositions of this invention may be incorporated into the composition as the product of the synthesis generating such components, either with or without an intermediate purification step. Where there is no purification step, commonly the mixture used will comprise the desired component or mixtures thereof (and percentages given herein relate to the weight percent of the component itself unless otherwise specified) and in addition unreacted starting materials and impurities formed from side reactions and/or incomplete reaction. For example, for an ethoxylated or substituted component, the mixture will likely comprise different degrees of ethoxylation/substitution.

EXAMPLES

Example 1

Deposition Test on Model Surfaces Using DPI

In order to illustrate the increase of deposition of a nuclease enzyme on a hydrophobised surface, the following experiment was carried out: using a Dual Polarized Interferometer (Farfield Analight Bio200) we recorded the deposition of the nuclease (SEQ ID NO 1) on two model surfaces.

First a neat quartz hydrophilic surface: An Anachip™ chip from Farfield was treated by exposing it to UV light for 30 minutes using a UV/Ozone Procleaner™ (Bioforce Nanosciences). The surface is then highly hydrophilic.

A second surface was hydrophobically modified: A UV-O3 treated Anachip™ was dipped in a 1% solution (Chloromethyl)trimethylsilane (Sigma Aldrich) in toluene for 30 seconds and rinsed with ethanol. This method grafts silane on the silica surface increasing the concentration of methyl groups on the surface, thus rendering it hydrophobic.

The treated chips were then placed in the DPI instrument and put in contact with a flow of deionised water to measure a baseline signal, once the initial signal is stable a solution of 2.6% in mass nuclease in deionised water is then injected and once the signal is stabilized, the surface was rinsed with de-ionised (DI) water. DPI measures the changes in refractive index on the surface, the difference between the pure DI water signal and the signal after the final rinse indicates nuclease retention. On the hydrophilic surface, the signal rose after the injection, due to the nuclease flowing above the surface. However, the change was modest, showing the minimal interaction of the nuclease with the surface. After rinsing with DI water the signal rapidly returned to the baseline, evidence that the nuclease has not deposited on the hydrophilic surface.

In the case of the hydrophobically modified surface, the signal raised considerably more after injection and took longer to stabilize compared to the hydrophilic surface. This indicates that the nuclease is depositing onto the surface and increasing coverage over time. After rinse, the signal remains higher than the DI water baseline due to retention of nuclease on the surface.

This experiment shows that the nuclease according to SEQ ID NO1 is retained of the hydrophobic surface more effectively than on the hydrophilic surface.

The following Formulation Examples illustrate cleaning compositions suitable for forming the aqueous liquor.

Formulation Examples

Examples 1-7

Heavy Duty Liquid Laundry Detergent Compositions

| Ingredients | 1 | 2 | 3 | 4 | 5 | 6 | 7 |
|---|---|---|---|---|---|---|---|
| | | | | % weight | | | |
| $AE_{1.8}S$ | 11.00 | 10.00 | 4.00 | 6.30 | — | — | — |
| $AE_3S$ | — | — | — | — | 2.40 | — | — |
| LAS | 1.40 | 4.00 | 8.00 | 3.30 | 5.00 | 8.00 | 19.00 |
| HSAS | 3.00 | 5.10 | 3.00 | — | — | — | — |
| AE9 | 0.4 | 0.6 | 0.3 | 0.3 | — | — | — |
| AE8 | — | — | — | — | — | — | 20.00 |
| AE7 | — | — | — | — | 2.40 | 6.00 | — |
| $C_{12-14}$ dimethyl Amine Oxide | 0.30 | 0.73 | 0.23 | 0.37 | — | — | — |
| $C_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI 1 | 0.32 | 0.05 | — | 0.60 | 0.10 | 0.60 | 0.01 |
| DTI 2 | 0.32 | 0.10 | 0.60 | 0.60 | 0.05 | 0.40 | 0.20 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.60 | 0.70 | 0.90 | 0.70 | 0.60 | 1.50 |
| Mannanase | 0.07 | 0.05 | 0.045 | 0.06 | 0.04 | 0.045 | 0.10 |
| Amylase 1 | 0.30 | — | 0.30 | 0.10 | — | 0.40 | 0.10 |
| Amylase 2 | — | 0.20 | 0.10 | 0.15 | 0.07 | — | 0.10 |
| Xyloglucannase | 0.20 | 0.10 | — | — | 0.05 | 0.05 | 0.20 |
| Lipase | 0.40 | 0.20 | 0.30 | 0.10 | 0.20 | — | — |
| Polishing enzyme | — | 0.04 | — | — | — | 0.004 | — |
| Nuclease (SEQ ID NO 1, 100% active) | 0.05 | 0.03 | 0.01 | 0.03 | 0.03 | 0.003 | 0.003 |
| Dispersin B | — | — | — | 0.05 | 0.03 | 0.001 | 0.001 |

-continued

| Ingredients | 1 | 2 | 3 | 4 % weight | 5 | 6 | 7 |
|---|---|---|---|---|---|---|---|
| Acid Violet 50 | 0.05 | — | — | — | — | — | 0.005 |
| Direct Violet 9 | — | — | — | — | — | 0.05 | — |
| Violet DD | — | 0.035 | 0.02 | 0.037 | 0.04 | — | — |
| Water, dyes & minors | | | | Balance | | | |
| pH | | | | 8.2 | | | |

Based on total cleaning and/or treatment composition weight.
Enzyme levels are reported as raw material.

Examples 8 to 16

Unit Dose Compositions

These examples provide various formulations for unit dose laundry detergents. Compositions 8 to 12 comprise a single unit dose compartment. The film used to encapsulate the compositions in PVA.

| Ingredients | 8 | 9 | 10 % weight | 11 | 12 |
|---|---|---|---|---|---|
| LAS | 14.5 | 14.5 | 14.5 | 14.5 | 14.5 |
| AE3S | 7.5 | 7.5 | 7.5 | 7.5 | 7.5 |
| AE7 | 13.0 | 13.0 | 13.0 | 13.0 | 13.0 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI 1 | 0.10 | — | 0.20 | 0.01 | 0.05 |
| DTI 2 | — | 0.10 | 0.20 | 0.25 | 0.05 |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulphonate | — | — | — | — | 2.0 |
| Protease | 0.80 | 0.60 | 0.07 | 1.00 | 1.50 |
| Mannanase | 0.07 | 0.05 | 0.05 | 0.10 | 0.01 |
| Amylase 1 | 0.20 | 0.11 | 0.30 | 0.50 | 0.05 |
| Amylase 2 | 0.11 | 0.20 | 0.10 | — | 0.50 |
| Polishing enzyme | 0.005 | 0.05 | — | — | — |
| Nuclease | 0.005 | 0.05 | 0.005 | 0.010 | 0.005 |
| Dispersin B | 0.010 | 0.05 | 0.005 | 0.005 | — |
| cyclohexyl dimethanol | — | — | — | 2.0 | — |
| Acid violet 50 | 0.03 | 0.02 | | | |
| Violet DD | | | 0.01 | 0.05 | 0.02 |
| Structurant | 0.14 | 0.14 | 0.14 | 0.14 | 0.14 |
| Perfume | 1.9 | 1.9 | 1.9 | 1.9 | 1.9 |
| Water and miscellaneous | | | To 100% | | |
| pH | | | 7.5-8.2 | | |

Based on total cleaning and/or treatment composition weight. Enzyme levels are reported as raw material.

In the following examples the unit dose has three compartments, but similar compositions can be made with two, four or five compartments. The film used to encapsulate the compartments is polyvinyl alcohol.

| Ingredients | Base compositions | | | |
|---|---|---|---|---|
| | 13 | 14 % weight | 15 | 16 |
| HLAS | 24.6 | 18.4 | 17.0 | 14.8 |
| AE7 | 20.1 | 14.3 | 13.0 | 18.6 |
| Citric Acid | 0.5 | 0.7 | 0.6 | 0.5 |
| C12-15 Fatty acid | 16.4 | 6.0 | 11.0 | 13.0 |
| Polymer 1 | 2.9 | 0.1 | — | — |
| Polymer 3 | 1.1 | 5.1 | 2.5 | 4.2 |
| Cationic cellulose polymer | — | — | 0.3 | 0.5 |
| Random graft copolymer | — | 1.5 | 0.3 | 0.2 |
| Chelant 2 | 1.1 | 2.0 | 0.6 | 1.5 |
| Optical Brightener 1 | 0.20 | 0.25 | 0.01 | 0.005 |
| Optical Brightener 3 | 0.18 | 0.09 | 0.30 | 0.005 |
| DTI 1 | 0.1 | — | 0.2 | — |
| DTI 2 | — | 0.1 | 0.2 | — |
| Glycerol | 5.3 | 5.0 | 5.0 | 4.2 |
| Monoethanolamine | 10.0 | 8.1 | 8.4 | 7.6 |
| Polyethylene glycol | — | — | 2.5 | 3.0 |
| Potassium sulfite | 0.2 | 0.3 | 0.5 | 0.7 |
| Protease | 0.80 | 0.60 | 0.40 | 0.80 |
| Amylase 1 | 0.20 | 0.20 | 0.200 | 0.30 |
| Polishing enzyme | — | — | 0.005 | 0.005 |
| Nuclease | 0.05 | 0.010 | 0.005 | 0.005 |
| Dispersin B | — | 0.010 | 0.010 | 0.010 |
| MgCl$_2$ | 0.2 | 0.2 | 0.1 | 0.3 |
| Structurant | 0.2 | 0.1 | 0.2 | 0.2 |
| Acid Violet 50 | 0.04 | 0.03 | 0.05 | 0.03 |
| Perfume/encapsulates | 0.10 | 0.30 | 0.01 | 0.05 |
| *Solvents and misc. | | To 100% | | |
| pH | | 7.0-8.2 | | |

| | Unit Dose Compositions | | | | | |
|---|---|---|---|---|---|---|
| | 17 | | | 18 | | |
| Compartment | A | B | C | A | B | C |
| Volume of each compartment | 40 ml | 5 ml | 5 ml | 40 ml | 5 ml | 5 ml |
| Ingredients | Active material in Wt. % | | | | | |
| Perfume | 1.6 | 1.6 | 1.6 | 1.6 | 1.6 | 1.6 |
| Violet DD | 0 | 0.006 | 0 | 0 | 0.004 | — |
| TiO2 | — | — | 0.1 | — | — | 0.1 |
| Sodium Sulfite | 0.4 | 0.4 | 0.4 | 0.3 | 0.3 | 0.3 |
| Polymer 5 | — | — | 2 | — | — | — |
| Hydrogenated castor oil | 0.14 | 0.14 | 0.14 | 0.14 | 0.14 | 0.14 |
| Base Composition 13, 14, 15 or 16 | | | Add to 100% | | | |

Based on total cleaning and/or treatment composition weight, enzyme levels are reported as raw material.

Examples 19 to 24

Granular laundry detergent compositions for hand washing or washing machines, typically top-loading washing machines.

| Ingredient | 19 | 20 | 21 % weight | 22 | 23 | 24 |
|---|---|---|---|---|---|---|
| LAS | 20 | 22 | 20 | 15 | 19.5 | 20 |
| Quaternary ammonium | 0.7 | 0.2 | 1.0 | 0.6 | — | — |
| AE3S | 0.9 | 1.0 | 0.9 | — | 0.4 | 0.9 |
| AE7 | — | — | — | 1.0 | 0.1 | 3.0 |

-continued

| Ingredient | 19 | 20 | 21 | 22 | 23 | 24 |
|---|---|---|---|---|---|---|
| | | | % weight | | | |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6R | 7.0 | 5.0 | 2.0 | 3.0 | 3.0 | 5.0 |
| Sodium carbonate | 20.0 | 17.0 | 23.0 | 14.0 | 14.0 | 16.0 |
| Polyacrylate MW 4500 | 1.0 | 0.6 | 1.0 | 1.0 | 1.5 | 1.0 |
| Random graft copolymer | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD | — | 0.03 | — | 0.03 | — | 0.03 |
| Protease 2 | 0.10 | 0.10 | 0.10 | 0.10 | — | 0.10 |
| Amylase | 0.03 | — | 0.03 | 0.03 | 0.03 | 0.03 |
| Lipase | 0.03 | 0.07 | 0.30 | 0.10 | 0.07 | 0.40 |
| Polishing enzyme | 0.002 | — | 0.05 | — | 0.02 | — |
| Nuclease | 0.001 | 0.001 | 0.01 | 0.05 | 0.002 | 0.02 |
| Dispersin B | 0.001 | 0.001 | 0.05 | — | 0.001 | — |
| Optical Brightener 1 | 0.200 | 0.001 | 0.300 | 0.650 | 0.050 | 0.001 |
| Optical Brightener 2 | 0.060 | — | 0.650 | 0.180 | 0.200 | 0.060 |
| Optical Brightener 3 | 0.100 | 0.060 | 0.050 | — | 0.030 | 0.300 |
| Chelant 1 | 0.60 | 0.80 | 0.60 | 0.25 | 0.60 | 0.60 |
| DTI 1 | 0.32 | 0.15 | 0.15 | — | 0.10 | 0.10 |
| DTI 2 | 0.32 | 0.15 | 0.30 | 0.30 | 0.10 | 0.20 |
| Sodium Percarbonate | — | 5.2 | 0.1 | — | — | — |
| Sodium Perborate | 4.4 | — | 3.85 | 2.09 | 0.78 | 3.63 |
| Nonanoyloxy benzensulphonate | 1.9 | 0.0 | 1.66 | 0.0 | 0.33 | 0.75 |
| Tetraacetylethylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC | 0.1 | 0.0 | 0.0 | 0.0 | 0.06 | 0.0 |
| Sulfate/Moisture | | | Balance | | | |

Examples 25-37

Granular laundry detergent compositions typically for front-loading automatic washing machines.

| Ingredient | 25 | 26 | 27 | 28 | 29 | 30 |
|---|---|---|---|---|---|---|
| | | | % weight | | | |
| LAS | 8.0 | 7.1 | 7.0 | 6.5 | 7.5 | 7.5 |
| AE3S | — | 4.8 | 1.0 | 5.2 | 4.0 | 4.0 |
| AS | 1.0 | — | 1.0 | — | — | — |
| AE7 | 2.2 | — | 2.2 | — | — | — |
| Quaternary ammonium | 0.75 | 0.94 | 0.98 | 0.98 | — | — |
| Crystalline layered silicate | 4.1 | — | 4.8 | — | — | — |
| Zeolite A | 5.0 | — | 2.0 | — | 2.0 | 2.0 |
| Citric acid | 3.0 | 4.0 | 3.0 | 4.0 | 2.5 | 3.0 |
| Sodium carbonate | 11.0 | 17.0 | 12.0 | 15.0 | 18.0 | 18.0 |
| Sodium silicate 2R | 0.08 | — | 0.11 | — | — | — |
| Optical Brightener 1 | — | 0.25 | 0.05 | 0.01 | 0.10 | 0.02 |
| Optical Brightener 2 | — | — | 0.25 | 0.20 | 0.01 | 0.08 |

-continued

| Ingredient | 25 | 26 | 27 | 28 | 29 | 30 |
|---|---|---|---|---|---|---|
| | | | % weight | | | |
| Optical Brightener 3 | — | 0.06 | 0.04 | 0.15 | — | 0.05 |
| DTI 1 | 0.08 | — | 0.04 | — | 0.10 | 0.01 |
| DTI 2 | 0.08 | — | 0.04 | 0.10 | 0.10 | 0.02 |
| Soil release agent | 0.75 | 0.72 | 0.71 | 0.72 | — | — |
| Acrylic/maleic acid copolymer | 1.1 | 3.7 | 1.0 | 3.7 | 2.6 | 3.8 |
| Carboxymethyl cellulose | 0.2 | 1.4 | 0.2 | 1.4 | 1.0 | 0.5 |
| Protease 3 | 0.20 | 0.20 | 0.30 | 0.15 | 0.12 | 0.13 |
| Amylase 3 | 0.20 | 0.15 | 0.20 | 0.30 | 0.15 | 0.15 |
| Lipase | 0.05 | 0.15 | 0.10 | — | — | — |
| Amylase 2 | 0.03 | 0.07 | — | — | 0.05 | 0.05 |
| Cellulase 2 | — | — | — | — | 0.10 | 0.10 |
| Polishing enzyme | 0.003 | 0.005 | 0.020 | — | — | — |
| Nuclease | 0.002 | 0.010 | 0.020 | 0.020 | 0.010 | 0.003 |
| Dispersin B | 0.002 | 0.010 | 0.020 | 0.020 | 0.010 | 0.002 |
| Tetraacetylethylenediamine | 3.6 | 4.0 | 3.6 | 4.0 | 2.2 | 1.4 |
| Sodium percarbonate | 13.0 | 13.2 | 13.0 | 13.2 | 16.0 | 14.0 |
| Chelant 3 | — | 0.2 | — | 0.2 | — | 0.2 |
| Chelant 2 | 0.2 | — | 0.2 | — | 0.2 | 0.2 |
| MgSO$_4$ | — | 0.42 | — | 0.42 | — | 0.4 |
| Perfume | 0.5 | 0.6 | 0.5 | 0.6 | 0.6 | 0.6 |
| Suds suppressor agglomerate | 0.05 | 0.10 | 0.05 | 0.10 | 0.06 | 0.05 |
| Soap | 0.45 | 0.45 | 0.45 | 0.45 | — | — |
| Acid Violet 50 | 0.04 | — | 0.05 | — | 0.04 | — |
| Violet DD | — | 0.04 | — | 0.05 | — | 0.04 |
| S-ACMC | 0.01 | 0.01 | — | 0.01 | — | — |
| Direct Violet 9 (active) | — | — | 0.0001 | 0.0001 | — | — |
| Sulfate/Water & Miscellaneous | | | Balance | | | |

AE1.8S is $C_{12-15}$ alkyl ethoxy (1.8) sulfate
AE3S is $C_{12-15}$ alkyl ethoxy (3) sulfate
AE7 is $C_{12-13}$ alcohol ethoxylate, with an average degree of ethoxylation of 7
AE8 is $C_{12-13}$ alcohol ethoxylate, with an average degree of ethoxylation of 8
AE9 is $C_{12-13}$ alcohol ethoxylate, with an average degree of ethoxylation of 9
Amylase 1 Stainzyme®, 15 mg active/g
Amylase 2 Natalase®, 29 mg active/g
Amylase 3 Stainzyme Plus®, 20 mg active/g,
AS is $C_{12-14}$ alkylsulfate
Cellulase 2 Celluclean™, 15.6 mg active/g
Xyloglucanase, Whitezyme®, 20 mg active/g
Chelant 1 diethylene triamine pentaacetic acid
Chelant 2 1-hydroxyethane 1,1-diphosphonic acid
Chelant 3 Na salt of Ethylenediamine-N,N'-disuccinic acid, (S,S) isomer (EDDS)
Dispersin B Glycosidase hydrolase, reported as 1000 mg active/g
DTI 1 is poly(4-vinylpyridine-1-oxide) (such as Chromabond S-403E®),
DTI 2 is poly(1-vinylpyrrolidone-co-1-vinylimidazole) (such as Sokalan HP56®).
HSAS is mid-branched alkyl sulfate as disclosed in U.S. Pat. Nos. 6,020,303 and 6,060,443
LAS is linear alkylbenzenesulfonate having an average aliphatic carbon chain length $C_9$-$C_{15}$ (HLAS is acid form).

Lipase Lipex®, 18 mg active/g
Mannanase Mannaway®, 25 mg active/g
Nuclease phosphodiesterase SEQ ID NO 1, reported as 1000 mg active/g
Optical Brightener 1 is disodium 4,4'-bis{[4-anilino-6-morpholino-s-triazin-2-yl]-amino}-2,2'-stilbenedisulfonate
Optical Brightener 2 is disodium 4,4'-bis-(2-sulfostyryl) biphenyl (sodium salt)
Optical Brightener 3 is Optiblanc SPL10® from 3V Sigma
Perfume encapsulate: is a Core—shell melamine formaldehyde perfume microcapsules.
Photobleach Sulphonated zinc phthalocyanine
Polishing enzyme Paranitrobenzyl esterases, reported as 1000 mg active/g
Polymer 1 bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n=20-30, x=3 to 8 or sulphated or sulphonated variants thereof
Polymer 2 Ethoxylated ($EO_{15}$) tetraethylene pentamine
Polymer 3 Ethoxylated Polyethylenimine
Polymer 4 Ethoxylated hexamethylene diamine
Polymer 5 Acusol 305, Rohm&Haas
Protease Purafect Prime®, 40.6 mg active/g
Protease 2 Savinase®, 32.89 mg active/g
Protease 3 Purafect®, 84 mg active/g
Quaternary ammonium is $C_{12-14}$ Dimethylhydroxyethyl ammonium chloride
S-ACMC Reactive Blue 19 Azo-CM-Cellulose provided by Megazyme
Structurant Hydrogenated Castor Oil The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a textile comprising the steps of:
   (i) providing a hydrophobically-modified textile;
   (ii) contacting the textile from step (i) with an aqueous solution consisting of a nuclease enzyme.

2. A method according to claim 1, wherein the nuclease enzyme is present at a concentration of from about 0.01 ppm to about 1000 ppm.

3. A method according to claim 1 wherein the nuclease is selected from any of E.C. classes E.C. 3.1.21.x (where x=1, 2, 3, 4, 5, 6, 7, 8, 9), 3.1.22.y (where y=1, 2, 4, 5), E.C. 3.1.30.z (where z=1, 2) or E.C. 3.1.31.1, or mixtures thereof.

4. A method according to claim 3 wherein the nuclease is selected from E.C. class E.C. 3.1.21.1.

5. A method according to claim 1 wherein the nuclease enzyme comprises a deoxyribonuclease.

6. A method according to claim 2 in which the enzyme comprises an enzyme having both RNase and DNase activity.

7. A method according to claim 6 in which the enzyme is from E.C. 3. 1.30.2.

8. A method according to claim 1 wherein the enzyme is a microbial enzyme.

9. A method according to claim 8 wherein the enzyme is a bacterial enzyme.

10. A method according to claim 1 wherein the enzyme has an amino acid sequence having at least about 85% identity with the amino acid sequence shown in SEQ ID NO:1, SEQ ID NO:2 or SEQ ID NO:3.

11. A method according to claim 1 wherein the textile comprises a blended textile comprising polyester.

12. A method according to claim 1 wherein following step (ii) there is a rinsing and drying step.

13. A method according to claim 1 wherein the hydrophobic modification of the textile is in the form of a finishing step provided in textile manufacturing.

14. A method according to claim 1 wherein the hydrophobic modification of the textile is in the form of a finishing step provided in the textile manufacturing comprising applying a cationic compound, silicone, paraffin or fluorinated compound to the textile.

* * * * *

SEQUENCE LISTING

```
<160> NUMBER OF SEQ ID NOS: 6

<210> SEQ ID NO 1
<211> LENGTH: 109
<212> TYPE: PRT
<213> ORGANISM: Bacillus licheniformis

<400> SEQUENCE: 1

Ala Arg Tyr Asp Asp Val Leu Tyr Phe Pro Ala Ser Arg Tyr Pro Glu
1               5                   10                  15

Thr Gly Ala His Ile Ser Asp Ala Ile Lys Ala Gly His Ala Asp Val
            20                  25                  30

Cys Thr Ile Glu Arg Ser Gly Ala Asp Lys Arg Arg Gln Glu Ser Leu
        35                  40                  45

Lys Gly Ile Pro Thr Lys Pro Gly Phe Asp Arg Asp Glu Trp Pro Met
    50                  55                  60

Ala Met Cys Glu Glu Gly Lys Gly Ala Ser Val Arg Tyr Val Ser
65                  70                  75                  80

Ser Ser Asp Asn Arg Gly Ala Gly Ser Trp Val Gly Asn Arg Leu Asn
                85                  90                  95

Gly Tyr Ala Asp Gly Thr Arg Ile Leu Phe Ile Val Gln
            100                 105

<210> SEQ ID NO 2
<211> LENGTH: 109
<212> TYPE: PRT
<213> ORGANISM: Bacillus subtilis

<400> SEQUENCE: 2

Ala Ser Ser Tyr Asp Lys Val Leu Tyr Phe Pro Leu Ser Arg Tyr Pro
1               5                   10                  15

Glu Thr Gly Ser His Ile Arg Asp Ala Ile Ala Glu Gly His Pro Asp
            20                  25                  30
```

Ile Cys Thr Ile Asp Asp Gly Ala Asp Lys Arg Arg Glu Glu Ser Leu
         35                  40                  45

Lys Gly Ile Pro Thr Lys Pro Gly Tyr Asp Arg Asp Glu Trp Pro Met
 50                  55                  60

Ala Val Cys Glu Glu Gly Ala Gly Ala Asp Val Arg Tyr Val Thr
 65                  70                  75                  80

Pro Ser Asp Asn Arg Gly Ala Gly Ser Trp Val Gly Asn Gln Met Ser
                 85                  90                  95

Ser Tyr Pro Asp Gly Thr Arg Val Leu Phe Ile Val Gln
                100                 105

<210> SEQ ID NO 3
<211> LENGTH: 109
<212> TYPE: PRT
<213> ORGANISM: Bacillus licheniformis

<400> SEQUENCE: 3

Ala Arg Tyr Asp Asp Ile Leu Tyr Phe Pro Ala Ser Arg Tyr Pro Glu
 1               5                  10                  15

Thr Gly Ala His Ile Ser Asp Ala Ile Lys Ala Gly His Ser Asp Val
                20                  25                  30

Cys Thr Ile Glu Arg Ser Gly Ala Asp Lys Arg Arg Gln Glu Ser Leu
         35                  40                  45

Lys Gly Ile Pro Thr Lys Pro Gly Phe Asp Arg Asp Glu Trp Pro Met
 50                  55                  60

Ala Met Cys Glu Glu Gly Gly Lys Gly Ala Ser Val Arg Tyr Val Ser
 65                  70                  75                  80

Ser Ser Asp Asn Arg Gly Ala Gly Ser Trp Val Gly Asn Arg Leu Ser
                 85                  90                  95

Gly Phe Ala Asp Gly Thr Arg Ile Leu Phe Ile Val Gln
                100                 105

<210> SEQ ID NO 4
<211> LENGTH: 361
<212> TYPE: PRT
<213> ORGANISM: Aggregatibacter actinomycetemcomitans

<400> SEQUENCE: 4

Asn Cys Cys Val Lys Gly Asn Ser Ile Tyr Pro Gln Lys Thr Ser Thr
 1               5                  10                  15

Lys Gln Thr Gly Leu Met Leu Asp Ile Ala Arg His Phe Tyr Ser Pro
                20                  25                  30

Glu Val Ile Lys Ser Phe Ile Asp Thr Ile Ser Leu Ser Gly Gly Asn
         35                  40                  45

Phe Leu His Leu His Phe Ser Asp His Glu Asn Tyr Ala Ile Glu Ser
 50                  55                  60

His Leu Leu Asn Gln Arg Ala Glu Asn Ala Val Gln Gly Lys Asp Gly
 65                  70                  75                  80

Ile Tyr Ile Asn Pro Tyr Thr Gly Lys Pro Phe Leu Ser Tyr Arg Gln
                 85                  90                  95

Leu Asp Asp Ile Lys Ala Tyr Ala Lys Ala Lys Gly Ile Glu Leu Ile
                100                 105                 110

Pro Glu Leu Asp Ser Pro Asn His Met Thr Ala Ile Phe Lys Leu Val
            115                 120                 125

Gln Lys Asp Arg Gly Val Lys Tyr Leu Gln Gly Leu Lys Ser Arg Gln
130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
            165                 170                 175

His Phe His Ile Gly Gly Asp Glu Phe Gly Tyr Ser Val Glu Ser Asn
        180                 185                 190

His Glu Phe Ile Thr Tyr Ala Asn Lys Leu Ser Tyr Phe Leu Glu Lys
    195                 200                 205

Lys Gly Leu Lys Thr Arg Met Trp Asn Asp Gly Leu Ile Lys Asn Thr
210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
            245                 250                 255

Val Ser Leu Pro Glu Leu Leu Ala Lys Gly Phe Thr Val Leu Asn Tyr
        260                 265                 270

Asn Ser Tyr Tyr Leu Tyr Ile Val Pro Lys Ala Ser Pro Thr Phe Ser
    275                 280                 285

Gln Asp Ala Ala Phe Ala Ala Lys Asp Val Ile Lys Asn Trp Asp Leu
290                 295                 300

Gly Val Trp Asp Gly Arg Asn Thr Lys Asn Arg Val Gln Asn Thr His
305                 310                 315                 320

Glu Ile Ala Gly Ala Leu Ser Ile Trp Gly Glu Asp Ala Lys Ala
            325                 330                 335

Leu Lys Asp Glu Thr Ile Gln Lys Asn Thr Lys Ser Leu Leu Glu Ala
        340                 345                 350

Val Ile His Lys Thr Asn Gly Asp Glu
    355                 360

<210> SEQ ID NO 5
<211> LENGTH: 204
<212> TYPE: PRT
<213> ORGANISM: Aspergillus oryzae

<400> SEQUENCE: 5

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
            20                  25                  30

Ile Leu Cys Lys Gly Ala Pro Asn Val Leu Gln Arg Val Asn Glu Lys
        35                  40                  45

Thr Lys Asn Ser Asn Arg Asp Arg Ser Gly Ala Asn Lys Gly Pro Phe
    50                  55                  60

Lys Asp Pro Gln Lys Trp Gly Ile Lys Ala Leu Pro Pro Lys Asn Pro
65                  70                  75                  80

Ser Trp Ser Ala Gln Asp Phe Lys Ser Pro Glu Glu Tyr Ala Phe Ala
            85                  90                  95

Ser Ser Leu Gln Gly Gly Thr Asn Ala Ile Leu Ala Pro Val Asn Leu
        100                 105                 110

Ala Ser Gln Asn Ser Gln Gly Gly Val Leu Asn Gly Phe Tyr Ser Ala
    115                 120                 125

Asn Lys Val Ala Gln Phe Asp Pro Ser Lys Pro Gln Gln Thr Lys Gly
130                 135                 140

Thr Trp Phe Gln Ile Thr Lys Phe Thr Gly Ala Ala Gly Pro Tyr Cys
145                 150                 155                 160

-continued

```
Lys Ala Leu Gly Ser Asn Asp Lys Ser Val Cys Asp Lys Asn Lys Asn
                165                 170                 175
Ile Ala Gly Asp Trp Gly Phe Asp Pro Ala Lys Trp Ala Tyr Gln Tyr
                180                 185                 190
Asp Glu Lys Asn Asn Lys Phe Asn Tyr Val Gly Lys
            195                 200

<210> SEQ ID NO 6
<211> LENGTH: 188
<212> TYPE: PRT
<213> ORGANISM: Trichoderma harzianum

<400> SEQUENCE: 6

Ala Pro Ala Pro Met Pro Thr Pro Pro Gly Ile Pro Thr Glu Ser Ser
1               5                   10                  15
Ala Arg Thr Gln Leu Ala Gly Leu Thr Val Ala Val Ala Gly Ser Gly
                20                  25                  30
Thr Gly Tyr Ser Arg Asp Leu Phe Pro Thr Trp Asp Ala Ile Ser Gly
            35                  40                  45
Asn Cys Asn Ala Arg Glu Tyr Val Leu Lys Arg Asp Gly Glu Gly Val
    50                  55                  60
Gln Val Asn Asn Ala Cys Glu Ser Gln Ser Gly Thr Trp Ile Ser Pro
65                  70                  75                  80
Tyr Asp Asn Ala Ser Phe Thr Asn Ala Ser Ser Leu Asp Ile Asp His
                85                  90                  95
Met Val Pro Leu Lys Asn Ala Trp Ile Ser Gly Ala Ser Ser Trp Thr
                100                 105                 110
Thr Ala Gln Arg Glu Ala Leu Ala Asn Asp Val Ser Arg Pro Gln Leu
            115                 120                 125
Trp Ala Val Ser Ala Ser Ala Asn Arg Ser Lys Gly Asp Arg Ser Pro
        130                 135                 140
Asp Gln Trp Lys Pro Pro Leu Thr Ser Phe Tyr Cys Thr Tyr Ala Lys
145                 150                 155                 160
Ser Trp Ile Asp Val Lys Ser Phe Tyr Lys Leu Thr Ile Thr Ser Ala
                165                 170                 175
Glu Lys Thr Ala Leu Ser Ser Met Leu Asp Thr Cys
            180                 185
```